(12) United States Patent
El-Sagheer et al.

(10) Patent No.: US 10,138,512 B2
(45) Date of Patent: Nov. 27, 2018

(54) NUCLEIC ACID PROCESSING OF A NUCLEIC ACID FRAGMENT WITH A TRIAZOLE LINKAGE

(71) Applicant: ATDBio Limited, Southampton (GB)

(72) Inventors: Afaf H. El-Sagheer, Hampshire (GB); Tom Brown, Hampshire (GB)

(73) Assignee: ATDBIO LIMITED, Southhampton (GB)

( * ) Notice: Subject to any disclaimer, the term of this patent is extended or adjusted under 35 U.S.C. 154(b) by 0 days.

(21) Appl. No.: 15/312,313

(22) PCT Filed: May 18, 2015

(86) PCT No.: PCT/GB2015/051451
§ 371 (c)(1),
(2) Date: Nov. 18, 2016

(87) PCT Pub. No.: WO2015/177520
PCT Pub. Date: Nov. 26, 2015

(65) Prior Publication Data
US 2017/0088888 A1    Mar. 30, 2017

(30) Foreign Application Priority Data
May 19, 2014    (GB) .................................. 1408841.3

(51) Int. Cl.
| | | |
|---|---|---|
| *C12Q 1/68* | (2018.01) | |
| *C12Q 1/6855* | (2018.01) | |
| *C12Q 1/6853* | (2018.01) | |
| *C12Q 1/6806* | (2018.01) | |
| *C12Q 1/6869* | (2018.01) | |

(52) U.S. Cl.
CPC ......... *C12Q 1/6855* (2013.01); *C12Q 1/6806* (2013.01); *C12Q 1/6853* (2013.01); *C12Q 1/6869* (2013.01)

(58) Field of Classification Search
CPC .................................................... C23Q 1/6855
USPC ....................................................... 435/6.12
See application file for complete search history.

(56) References Cited

U.S. PATENT DOCUMENTS

2013/0046083 A1    2/2013    Brown et al.

OTHER PUBLICATIONS

Vamvakopoulos Nucleic Acids Research vol. 4, No. 10 1977, pp. 3589-3597.*
Search Report for corresponding GB Application No. 1408841.3 dated May 12, 2015; 4 pages.
International Search Report for corresponding International Application No. PCT/GB2015/051451 dated Aug. 28, 2015; 4 pages.
Written Opinion of the International Searching Authority for corresponding International Application No. PCT/GB2015/051451 dated Aug. 28, 2015; 5 pages.
Agard et al., "Chemical approaches to perturb, profile, and perceive glycans," Accounts of Chemical Research (Jun. 2009) vol. 42, No. 6; 788-797.
Birts et al., "Transcription of click-linked DNA in human cells," Angew. Chem. Int. Ed. (Jan. 22, 2014) 53(9); 2362-2365.
Carthew et al., "Origins and mechanisms of miRNAs and siRNAs," Cell (Feb. 20, 2009) 136; 642-655.
Chapuis et al., "2'-lipid-modified oligonucleotides via a 'Staudinger-Vilarrasa' reaction," Tetrahedron Letters (2008) 49; 6838-6840.
Dallmann et al, "Structure and dynamics of triazole-linked DNA: Biocompatibility explained," Chem. Eur. J. (2011) 17; 14714-14717.
Dommerholt et al., "Readily accessible biocyclononynes for bioorthogonal labeling and three-dimensional imaging of living cells," Angew. Chem. Int. Ed. (2010) 49; 9422-9425.
Elbashir et al., "RNA interference is mediated by 21- and 22-nucleotide RNAs," Genes and Development (2001) 15; 188-200.
El-Sagheer et al., "Biocmpatible artificial DnA linker that is read through by DNA polymerases and is functional in *Escherichia coli*," PNAS (Jul. 12, 2011) vol. 108, No. 28; 11338-11343. XP55196445.
El-Sagheer et al., "Combined nucleobase and backbone modifications enhance DNA duplex stability and preserve biocompatibility," Chem. Sci. (2014) 5; 253-259.
El-Sagheer et al., "Efficient RNA synthesis by in vitro transcription of a tirazole-modified DNA template," Chem. Commun. (2011) 47; 12057-12058. XP55205663.
El-Sagheer et al., "Factors influencing hairpin oligonucleotide cyclization by the uncatalyzed alkyne-azide cycloaddition (AAC) reaction," Pure Appl. Chem. (2010) vol. 82, No. 8; 1599-1607.
El-Sagheer et al., "New strategy for the synthesis of chemically modified RNA constructs exemplified by hairpin and hammerhead ribozymes," PNAS (Aug. 31, 2010) vol. 107, No. 35; 15329-15334. XP55084941.
Fauster et al., "2'-azido RNA, a versatile tool for chemical biology: Synthesis, X-ray structure, siRNA applications, click labeling," ACS Chem. Biol. (2012) 7; 581-589.
Fujino et al., "Triazole-linked DNA as a primer surrogate in the synthesis of first-strand cDNA," Chem. Asian J. (2011) 6; 2956-2960.
Gerard et al., "Reverse transcriptase (EC 2.7.7.49)," Methods in Molecular Biology, vol. 16: Enzymes of Molecular Biology; 73-93.
Hafner et al., "Identification of microRNAs and other small regulatory RNAs using cDNA library sequencing," Methods (Jan. 2008) 44(1); 15 pages.
Hafner et al., "RNA-ligase-dependent biases in miRNA representation in deep-sequenced small RNA cDNA libraries," RNA (2011) 17; 1697-1712.
Huisgen, R., "Kinetics and mechanism of 1,3-dipolar cycloadditions," Angew. Chem. Internat. Edit. (1963) vol. 2, No. 11; 633-696.
Jayaprakash et al., "Identification and remediation of biases in the activity of RNA ligases in small-RNA deep sequencing," Nucleic Acids Research (2011); 1-12.

(Continued)

*Primary Examiner* — Jezia Riley
(74) *Attorney, Agent, or Firm* — Patterson Thuente Pedersen, P.A.

(57) ABSTRACT

A method of nucleic acid processing that comprises providing an adapted nucleic acid fragment having a triazole linkage therein, and transcribing the adapted nucleic acid fragment with reverse transcriptase. The invention further relates to kits and uses associated with the method.

19 Claims, 10 Drawing Sheets

Specification includes a Sequence Listing.

(56) References Cited

OTHER PUBLICATIONS

Kotewicz et al., "Isolation of cloned Moloney murine leukemia virus reverse transciptase lacking ribonuclease H activity," Nucleic Acids Research (1988) vol. 16, No. 1; 265-277.
Kumar et al., "Template-directed oligonucleotide strang ligation, covalent intramolecular DNA circularization and catenation using click chemistry," J. Am. Chem. Soc. (2007) 129; 6859-6864. XP002640516.
Linsen et al., "Limitations and possibilities of small RNA digital gene expression profiling," Nature Methods (Jul. 2009) vol. 6, No. 7; 474-476.
Mamanova et al., "Low-bias, strand-specific transcriptome Illumina sequencing by on-flowcell reverse transcription (FRT-seq)," Nature Protocols (Oct. 20, 2011) vol. 6, No. 11; 1736-1747.
Merczak et al., "Circular RNAs are a large class of animal RNAs with regulatory potentcy," Nature (Mar. 21, 2013) vol. 495; p. 333-342.
Miller et al., "Versatile 5'-functionaliztion of oligonucleotides on solid support: Amines, azides, thiols, and thioethers via phosphorus chemistry," J. Org. Chem. (2004) 69; 2404-2410.
Morin et al., "Application of massively parallel sequencing to microRNA profiling and discovery in human embryonic stem cells," Genome Research (2008) 18; 610-621.
Sanzone et al., "Assessing the biocompatibility of click-linked DNA in *Escherichia coil*," Nucleic Acids Research (2012) vol. 40, No. 20; 10568-10575.
Scolnick et al., "RNA-dependent DNA polymerase activity in five RNA viruses: Divalent cation requirements," PNAS (Dec. 1970) vol. 67, No. 4; 1789-1796.

Shelbourne et al., "Fast and efficient DNA crosslinking and multiple orthogonal labeling by copper-free click chemistry," Chem. Commun. (2012) 48; 11184-11186.
Shelbourne et al., "Fast copper-free click DNA ligation by the ring-strain promoted alkyne-azide cycloaddition reaction," Chem. Commun. (2011) 47; 6257-6259.
Sorefan et al., "Reducing ligation bias of small RNAs in libraries for next generation sequencing," Silence (2012) 3: 4; 11 pages.
Winz et al., "Site-specific terminal and internal labeling of RNA by poly(A) polymerase tailing and copper-catalyzed or copper-free strain-promoted click chemistry," Nucleic Acids Research (2012) vol. 40, No. 10, 13 pages.
Zhang et al., "Genome-wide analysis of small RNA and novel microRNA discovery in human acute lymphoblastic leukemia based on extensive sequencing approach," PLoS ONE (Sep. 2009) vol. 4, Issue 9, e6849-e; 10 pages.
Zhuang et al., "Small RNA expression profiling by high-throughput sequencing: Implications of enzymatic manipulation," Journal of Nucleic Acids (2012) vol. 2012; 15 pages.
Zhuang et al., "Structural bias in T4 RNA ligase-mediated 3'-adapter ligation," Nucleic Acids Research (2012) Vo. 40, No. 7; 14 pages.
GB Office Action for corresponding GB Application No. GB1619468. 0, dated Feb. 3, 2018, Inventor(s): El-Sagheer et al.; 4 pages.
EP Search Report for corresponding EP Application No. 15724010. 2, dated Dec. 7, 2017, Inventor(s): El-Sagheer et al.; 4 pages.
Hiroyuki Isobe et al: "Triazole-Linked Analogues of DNA and RNA (TL DNA and TL RNA): Synthesis and Functions : Triazole-Linked DNA and RNA Analogues", Chemical Record, vol. 14, No. 1, Dec. 19, 2013 (Dec. 19, 2013), pp. 41-51.

\* cited by examiner

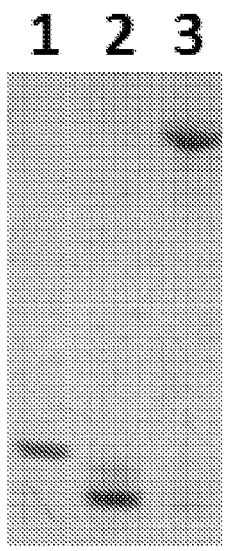
Figure 13
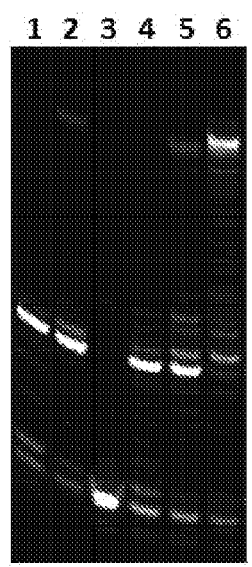
Figure 14
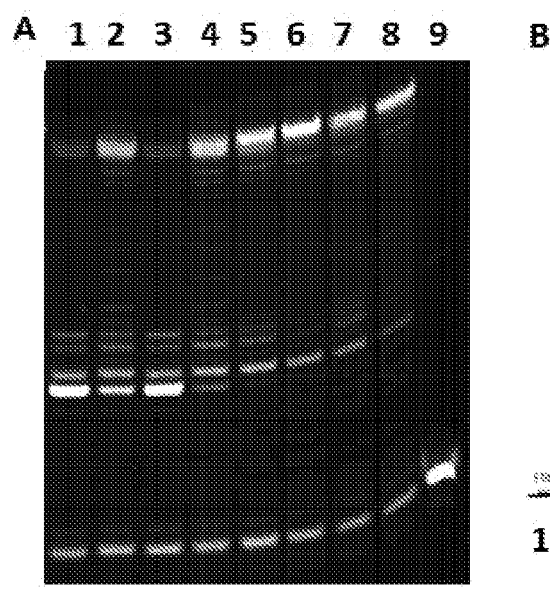
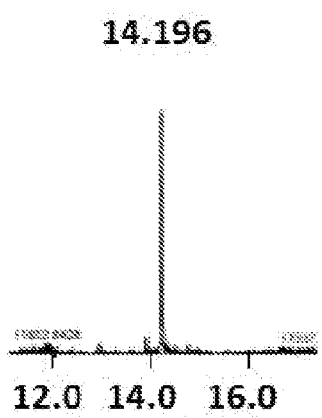
Figure 15

Figure 18

```
PCR.SEQ(1>47)                        CTGAACCGCTCTTCCGATCTNNACCCCTATCACGATTAGCATTAAA
ODN15-1_M13uni-21.ab1(17>823)    GCAGCTGAACCGCTCTTCCG-TCTGGACCCCTATCACGATTAGCATTAACTTAC  GoA
ODN15-3_M13uni-21.ab1(9>850)     GCAGCTGAACCGCTCTTCCGATCTGGACCCCTATCACGATTAGCATTAACTTAC  GoA
ODN15-4_M13uni-21.ab1(11>847)    GCAGCTGAACCGCTCTTCCGATCTGGACCCCTATCACGATTAGCATTAACTTAC  GoA
ODN19-4_M13uni-21.ab1(10>826)    GCAGCTGAACCGCTCTTCCGATCTG-ACCCCTATCACGATTAGCATTAACTTAC  (AC)
ODN19-2_M13uni-21.ab1(13>863)    GCAGCTGAACCGCTCTTCCGATCTG-ACCCCTATCACGATTAGCATTAACTTAC  (AC)
ODN19-3_M13uni-21.ab1(10>814)    GCAGCTGAACCGCTCTTCCGATCTG-ACCCCTATCACGATTAGCATTAACTTAC  (AC)
ODN20-4_M13uni-21.ab1(10>853)    GGCAGCTGAACCGCTCTTCCGATCTG-ACCCCTATCACGATTAGCATTAACTTA   (AC)
ODN20-1_M13uni-21.ab1(9>814)     GCAGCTGAACCGCTCTTCCGATCTG-A-CCCTATCACGATTAGCATTAACTTAC  (AC)
ODN20-2_M13uni-21.ab1(11>863)    GGCAGCTGAACCGCTCTTCCGATCTG-ACCCCTATCACGATTAGCATTAACTTA   (AC)
NN= GG or GA
```

NUCLEIC ACID PROCESSING OF A NUCLEIC ACID FRAGMENT WITH A TRIAZOLE LINKAGE

CROSS-REFERENCE TO RELATED APPLICATIONS

The present application is a National Phase entry of PCT Application No. PCT/GB2015/051451, filed on May 18, 2015, which claims priority to GB Patent Application No. 1408841.3, filed on May 19, 2014, which are hereby fully incorporated herein by reference.

FIELD OF THE INVENTION

The present invention relates to methods of nucleic acid processing, such as RNA sequencing. The present invention particularly relates to methods of nucleic acid processing of a nucleic acid fragment with a triazole linkage.

BACKGROUND OF THE INVENTION

Small RNAs are considered to play a very important role in regulation of chromatin structure, chromosome segregation, transcription, RNA processing, RNA stability, and translation. RNAs extracted from eukaryotic cells are classified into five different categories: ribosomal RNAs (rRNA), transfer RNAs (tRNA), messenger RNAs (mRNAs), long noncoding RNAs, and small RNAs. Over 90% of the total RNA molecules in the extract are rRNA and tRNA. Small RNAs account only for about 1% of the total RNA population, this include microRNAs (miRNAs), small interfering RNAs (siRNAs) and piwi-interacting RNAs (piRNAs).

High-throughput sequencing (HTS, or next generation sequencing) techniques such as Illumia®, SOLiD® (Sequencing by Oligonucleotide Ligation and Detection) and Roche 454 pyrosequencing, are playing very important role in novel small RNA detection and miRNA editing detection.

In order to generate RNA sequencing libraries, the isolated native RNA is usually reverse transcribed into DNA followed by PCR-amplification. The unknown RNAs therefore need to be ligated to a known sequence of two adaptors or handles, one at the 3'-end and the other at the 5'-end of the native RNA. The 3'-handle installation is often done either by poly-A tailing or by 3'-adaptor ligation catalyzed by a T4 RNA ligase. As small RNAs are just over 20 bases long, poly-A tailing will generate a great percentage of poly-A signal. It also has the disadvantage of the uncertainty about the origin of the poly-A region and is often followed by an additional parallel poly C tailing reaction, which further complicates the procedure. This technique is considered to be not suitable for small RNA sequencing. So the 3'-handle is normally provided by a 3'-adaptor.

The 3'-adaptor ligation and the 5'-adaptor ligation reactions need to be separated by a gel purification step, otherwise the excessive 3'-adaptor will ligate to the 5'-adaptor.

Sequencing bias of the small RNA profiling result generated by HTS has been reported and systematically studied. This bias, occurs because some target RNAs in the sample adopt secondary structure in presence of the ligation buffer, leading to different adaptor ligation efficiency. This results an uneven representation of the RNA population in the sequencing library. The bias affects the reliability of studies to measure the expression level of miRNAs. The 3'-adaptor ligation step conducted by T4 RNA ligase is the cause of major RNA sequencing bias.

Despite the drawback of using ligase in RNA sequencing methods, no practical alternative has replaced its use and practical methods of mitigating the ligation-mediated sequence bias are continually sought.

SUMMARY OF THE INVENTION

An aim of the present invention is to provide an improved method of nucleic acid processing, such as an improved method of small RNA sequencing which seeks to reduce the issue of ligation-mediated sequence bias.

In certain aspects, the present invention is directed at a method of nucleic acid processing that comprises providing an adapted nucleic acid fragment having a triazole linkage therein, and transcribing the adapted nucleic acid fragment with reverse transcriptase.

In certain aspects of the present invention, the triazole linkage is a result of $Cu^I$-catalysed [3+2] Azide-Alkyne Cycloaddition (CuAAC) reaction or a Strain-Promoted Alkyne Azide Cycloaddition (SPAAC) reaction.

In certain aspects of the present invention, the adapted nucleic acid fragment comprises a nucleic acid fragment linked to a 3'-adapter molecule by a triazole linkage.

In certain aspects of the present invention, the adapted nucleic acid fragment comprises a 5'-adapter molecule linked to the 5'-end of the nucleic acid fragment. In certain other aspects, the adapted nucleic acid fragment comprises RNA or a combination of RNA and other nucleic acid, or analogues thereof In certain aspects of the present invention, the method of the present invention comprises a method of nucleic acid sequencing, wherein the adapted nucleic acid fragment is provided by linking a 3'-adapter molecule to the 3' end of a nucleic acid fragment, thereby forming an adapted nucleic acid fragment, wherein the 3'-adapter molecule is linked to the nucleic acid fragment via a triazole linkage, and wherein the adapted nucleic acid fragment is transcribed by annealing a primer to the adapted nucleic acid fragment, which is complementary thereto, transcribing the adapted nucleic acid fragment using reverse transcriptase to form a cDNA strand, and further comprising determining the sequence of the cDNA strand.

In certain aspects of the present invention, the method further comprises linking a 5'-adapter molecule to the 5'-end of the nucleic acid fragment, optionally wherein the 5'-adapter molecule is linked to the 5'-end of the nucleic acid fragment by a ligase In certain aspects of the present invention, the 5'-adapter molecule is linked to the 5'-end of the nucleic acid fragment by a ligase.

In certain aspects of the present invention, the 3'-adapter molecule and/or 5'-adapter molecule have a known/predetermined sequence.

In certain aspects of the present invention, the sequence of the nucleic acid fragment is unknown prior to sequencing.

In certain aspects of the present invention, the nucleic acid fragment is RNA, optionally wherein the RNA comprises non-coding RNA (ncRNA). In certain other aspects, the RNA comprises non-coding RNA (ncRNA).

In certain aspects of the present invention, determining the sequence of the cDNA strand comprises amplifying the sequence of the cDNA strand in a PCR reaction, and analyzing the PCR product.

In certain aspects of the present invention, the triazole linkage comprises a 7 to 9 membered ring, and a triazole group. In certain aspects, the triazole linkage comprises Formula (I) or Formula (II):

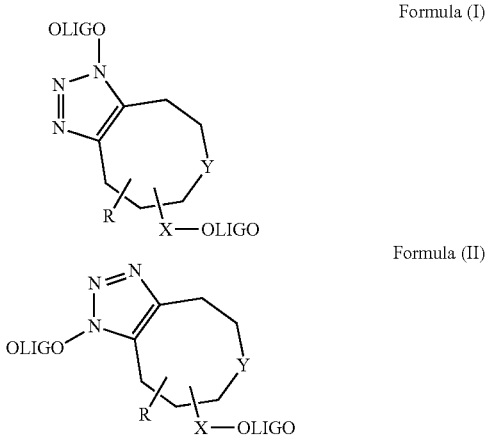

Formula (I)

Formula (II)

wherein X is a linker; Y is one or more carbon or heteroatoms; R is a substituent; and OLIGO is the 3'-adapter molecule or the nucleic acid fragment.

In certain aspects of the present invention, the adapted nucleic acid fragment comprising the triazole linkage comprises the Formula (III):

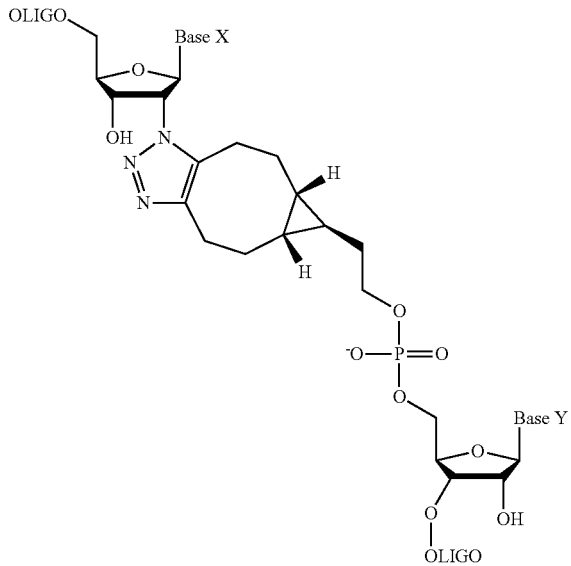

Formula (III)

wherein Base X is guanine, adenine, uracil, thymine or cytosine; Base Y is guanine, adenine, uracil, thymine or cytosine; and OLIGO is a nucleic acid fragment, or analogue thereof, or an adapter molecule.

In certain aspects of the present invention, the triazole linkage is formed by reacting an alkyne group on the nucleic acid fragment with an azide group on the 3'-adapter molecule; or by reacting an alkyne group on the 3'-adapter molecule with an azide group on the nucleic acid fragment.

In certain aspects of the present invention, the alkyne group comprises a cyclooctyne or dibenzocyclooctyne.

In certain aspects of the present invention, the linking of the 3'-adapter molecule to the nucleic acid fragment is carried out in metal-ion free conditions.

In certain aspects of the present invention, the reverse transcriptase is RNase H deficient.

In certain aspects of the present invention, the reverse transcription reaction uses a buffer comprising $Mn^{2+}$.

In certain aspects, the present invention is directed to the use of reverse transcriptase to transcribe nucleic acid comprising one or more triazole linkages.

In certain aspects, the present invention is directed to a kit for sequencing a nucleic acid fragment comprising a reverse transcriptase; and a 3'-adapter molecule having a reactive group arranged to form a triazole linkage with an opposing reactive group on the nucleic acid fragment. In certain other aspects of the present invention, the kit may comprise at least one of a 5'-adapter molecule; one or more primers for reverse transcriptase polymerisation; a nucleotidyl transferase; and a resin for a solid-phase phosphoramidite reaction for adding an alkyne group to the nucleic acid fragment or 3'-adapter molecule. In certain other aspects of the present invention, the kit may comprise one or more primers for reverse transcriptase polymerisation. In certain other aspects of the present invention, the kit may comprise a nucleotidyl transferase. In certain other aspects of the present invention, the kit may comprise a resin for a solid-phase phosphoramidite reaction for adding an alkyne group to the nucleic acid fragment or 3'-adapter molecule.

In certain aspects, the present invention is directed to nucleic acid processing, the use, or a kit, substantially as described herein, and optionally with reference to the following accompanying drawings.

BRIEF DESCRIPTION OF THE FIGURES

The invention can be completely understood in consideration of the following detailed description of various aspects and embodiments of the present invention in connection with the accompanying drawings, in which:

FIG. 13: 20% Polyacrylamide gel for non templated copper free click ligation to synthesize ODN20. Lane 1; 2'-azide oligo ODN23, lane 2, alkyne oligo ODN21, lane 3; crude reaction mixture.

FIG. 14: 20% polyacrylamide gel for reverse transcription of ODN20 (BCN R1) and ODN24 (BCN 1). Lane 1 and 2; reverse transcription of template ODN24 (BCN1) at 2 h and 18 h, lane 3; primer ODN7 (−7, P1); lane 4, 5 and 6 reverse transcription of template BCNR1 at 10 min, 2 h and 18 h. M-MuLV Reverse Transcriptase (RNase H−) was used.

FIG. 15: (A) 20% polyacrylamide gel for the effect of $Mg^{2+}$/$Mn^{2+}$ concentrations on the reverse transcription of ODN20 (BCN R1). Lane 1 and 2; incubation in 3 mM $Mg^{2+}$ for 2 h and 7 h respectively, lane 3 and 4; incubation in 10 mM $Mg^{2+}$ for 2 h and 7 h respectively, lane 5 and 6; incubation in 3 mM $Mn^{2+}$ for 2 h and 7 h respectively, lane 7 and 8; incubation in 10 mM $Mn^{2+}$ incubation for 2 h and 7 h respectively, lane 9; primer ODN7. (B) Mass spectrometry of the reverse transcription reaction of ODN20 (BCN R1), Cal mass 14196 for full length minus G.

FIG. 18: Shows the results of sequence analysis of sequences as determined by the method according to certain aspects of the present invention.

DETAILED DESCRIPTION OF THE PRESENT INVENTION

Figure 1:
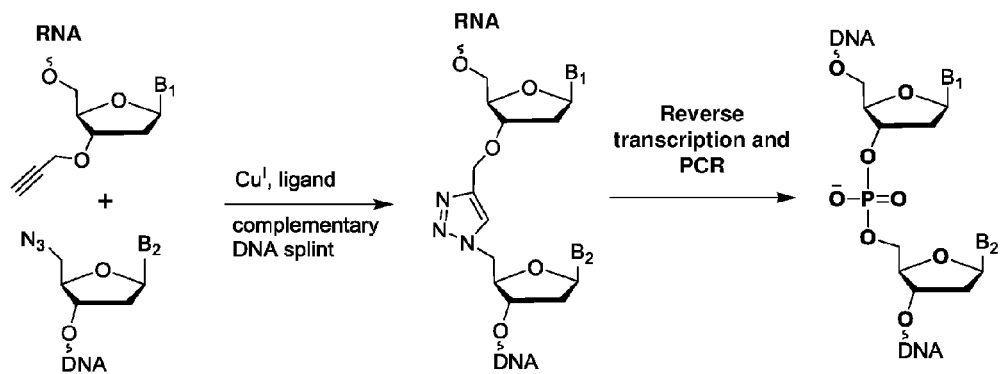
FIG. 1: shows a typical synthesis and PCR amplification of DNA containing an artificial triazole linkage.

According to a first aspect of the present invention, there is provided a method of nucleic acid processing comprising providing an adapted nucleic acid fragment having a triazole linkage therein; and transcribing the adapted nucleic acid fragment with reverse transcriptase.

The reverse transcriptase enzyme is capable of reading through a bulky triazole linkage in nucleic acid such as RNA in order to transcribe a copy of the nucleic acid. Such triazole linkages are formed through the process of chemical ligation methods, such as a $Cu^I$-catalysed [3+2] Azide-Alkyne Cycloaddition (CuAAC) reaction. Surprisingly, a more bulky backbone, synthesized by the Strain-Promoted Alkyne Azide Cycloaddition (SPAAC) reaction between azide and cyclooctyne-modified oligonucleotides (copper-free click ligation), is also read through by the reverse transcriptase. It is surprising that reverse transcriptase reads through bulky triazole linkages because the linkage is much larger than a normal phosphodiester linkage and would not be expected to be accepted at the active site of a polymerase enzyme.

Advantageously, changing the process of RNA ligation to chemical ligation could overcome the sequence bias problem. Chemical ligation can have other advantages over enzymatic ligation; it can be carried out on a large scale and it is compatible with a wide range of pH and salts and salt concentrations. Also, the ability to use a different method for ligation of adapter molecules at 3' and 5'ends means that a typical gel purification between two ligation steps can be avoided prior to RNA sequencing.

The triazole linkage may be a result of a copper-free SPAAC click reaction, which advantageously does not require copper catalysis. Therefore, unlike other copper-requiring chemical ligation methods that may result in the provision of a less bulky linking group, the copper free click ligation is compatible with large biomolecules such as RNA and can be carried out in any biologically compatible buffer. The presence of copper causes degradation of long DNA and RNA molecules, so the avoidance of copper is a major advantage. Copper-free click ligation of RNA can also be carried out in conditions under which RNA secondary structure is unstable (e.g. in water without salt).

The adapted nucleic acid fragment may comprise a nucleic acid fragment linked to a pair of adapter molecules, wherein one of the adapters is linked by a triazole linkage.

The adapted nucleic acid fragment may comprise RNA. The adapted nucleic acid fragment may comprise a combination of RNA and other nucleic acid, or analogues thereof. The adapted nucleic acid fragment may comprise any of the group comprising RNA; DNA; and a nucleic acid analogue; or combinations thereof.

In certain aspects, the present invention may comprise a method of nucleic acid sequencing, wherein the adapted nucleic acid fragment is provided by: linking a 3'-adapter molecule to the 3' end of a nucleic acid fragment, thereby forming an adapted nucleic acid fragment, wherein the 3'-adapter molecule is linked to the nucleic acid fragment via a triazole linkage; and wherein the adapted nucleic acid fragment is transcribed by annealing a primer to the adapted nucleic acid fragment, which is complementary thereto; transcribing the adapted nucleic acid fragment using reverse transcriptase to form a cDNA strand; and further comprising determining the sequence of the cDNA strand.

The method may further comprise linking a 5'-adapter molecule to the 5' end of the nucleic acid fragment. The 5'-adapter molecule may be linked to the nucleic acid fragment via phosphate, for example via the natural sugar-phosphate backbone of nucleic acid. The 5'-adapter molecule may be linked to the nucleic acid fragment by ligation. The ligation of the 5'adapter molecule may be enzymatic, for example by ligase, or chemical.

The 3'-adapter molecule may comprise or consist of any of the group comprising RNA; DNA; and a nucleic acid analogue; or combinations thereof. The 3'-adapter molecule may comprise or consist of RNA. The 3'-adapter molecule may have a known/pre-determined sequence.

The 5'-adapter molecule may comprise or consist of any of the group comprising RNA; DNA; and a nucleic acid analogue; or combinations thereof. The 5'-adapter molecule may comprise or consist of RNA. The 5'-adapter molecule may have a known/pre-determined sequence.

The sequence of the nucleic acid fragment may be unknown prior to sequencing. The nucleic acid fragment may be RNA. The RNA may be non-coding RNA (ncRNA). The nucleic acid fragment may be less than 200 nucleotides in length. The nucleic acid fragment may be less than 100 nucleotides in length. The nucleic acid fragment may be less than 50 nucleotides in length. The nucleic acid fragment may be less than 30 nucleotides in length. The nucleic acid fragment may be less than 20 nucleotides in length. The nucleic acid fragment may be between about 10 and about 400 nucleotides in length. The nucleic acid fragment may be between about 10 and about 200 nucleotides in length. The nucleic acid fragment may be between about 20 and about 200 nucleotides in length. The nucleic acid fragment may be between about 20 and about 100 nucleotides in length. The nucleic acid fragment may be between about 20 and about 50 nucleotides in length. The nucleic acid fragment may be about 20 or 22 nucleotides in length. In an alternative embodiment, the nucleic acid fragment may be at least 200 nucleotides in length.

Determining the sequence of the cDNA strand may comprise amplifying the sequence of the cDNA strand in a PCR reaction, and analyzing the PCR product. The PCR reaction may comprise the use of forward and reverse primers. The forward primer may comprise a sequence substantially or completely complementary to the 5' adapter molecule. The reverse primer may comprise a sequence substantially or completely equivalent to the sequence of the 3'-adapter molecule. The reverse primer may comprise a sequence substantially or completely equivalent to the sequence of the primer used for transcribing the adapted nucleic acid fragment using reverse transcriptase.

In an embodiment where the sequence of the nucleic acid fragment is unknown, the forward primer may comprise a sequence substantially or completely complementary to the 5'-adapter molecule. In an alternative embodiment where the sequence, or a part of the sequence, of the nucleic acid fragment is known the forward primer may comprise a sequence substantially or completely complementary to the nucleic acid fragment.

Analyzing the PCR product may comprise detecting specific base pair addition during polymerase-mediated synthesis of the PCR product.

It will be understood by the skilled person that the reverse transcriptase may omit a one or two residues during polymerisation at a site corresponding to the site of the triazole linkage, which would be taken into account when determining the sequence. In particular, the omission of residues would be expected and their identity may be determined from a known sequence surrounding the triazole linkage.

The triazole linkage may comprise a 7 to 9 membered ring. The triazole linkage may comprise a substituted 7 to 9 membered ring. The triazole linkage may comprise a 7 to 9 membered ring and a triazole group. The triazole linkage may comprise a cyclic compound having at least one heteroatom in the ring.

The triazole linkage may comprise Formula (I) or Formula (II):

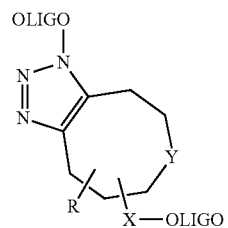

Formula (I)

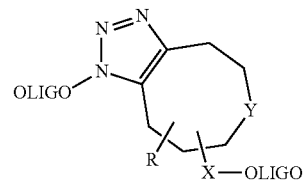

Formula (II)

wherein: X is a linker; Y is one or more carbon or heteroatoms; R is a substituent; and OLIGO is the 3'-adapter molecule or the nucleic acid.

In one embodiment the substituent may comprise one or more groups. The substituent groups may be electron-withdrawing groups. In one embodiment the ring may be fused with one or more conjugated rings, for example one or more benzene rings. In one embodiment the strained alkyne group may comprise a ring with a fluorine substituent.

The adapted nucleic acid fragment comprising the triazole linkage may comprise the Formula (III):

Formula (III)

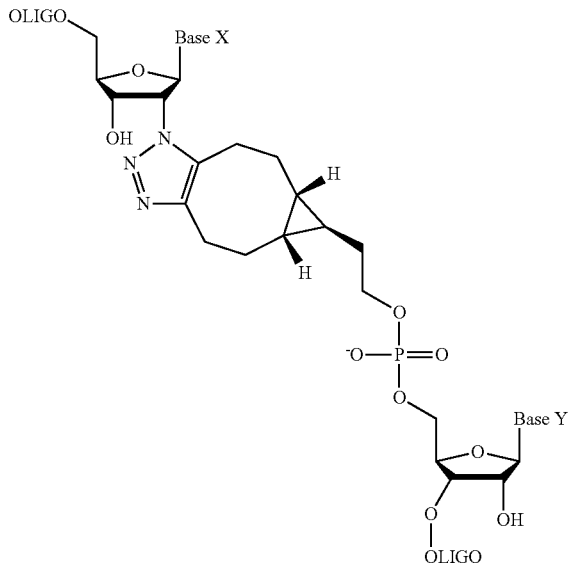

wherein: Base X is guanine, adenine, uracil, thymine or cytosine Base Y is guanine, adenine, uracil, thymine or cytosine; and OLIGO is a nucleic acid fragment, or analogue thereof, or an adapter molecule.

The nucleic acid fragment, analogue thereof, or adapter molecule may comprise DNA and/or RNA. The nucleic acid fragment, analogue thereof, or adapter molecule may comprise DNA, RNA PNA, LNA, GNA or TNA; or combinations thereof.

In an embodiment, base X and base Y may comprise cytosine. In an embodiment, base X may comprise cytosine. In an embodiment, base Y may comprise cytosine. In an embodiment, base X may comprise uracil and base Y may comprise cytosine.

The nucleotide bases flanking the triazole linkage may be $C_zC$. Advantageously the $C_zC$ linkage is more stable, providing an easier read-through for reverse transcriptase.

The triazole linkage may be formed by reacting an alkyne group on the nucleic acid fragment with an azide group on the 3'-adapter molecule. Alternatively, the triazole linkage may be formed by reacting an alkyne group on the 3'-adapter molecule with an azide group on the nucleic acid fragment.

The alkyne group may be a strained alkyne group. The linking of the 3'-adapter molecule to the nucleic acid fragment may be by use of a ring-strain promoted alkyne-azide [3+2] cycloaddition reaction, (a SPAAC reaction) between a strained alkyne and an azide group on the respective molecules to be linked.

The strained alkyne group and the azide group may react according to the following scheme:

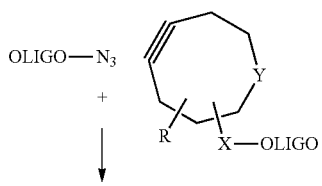

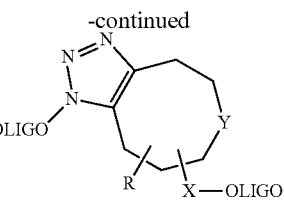

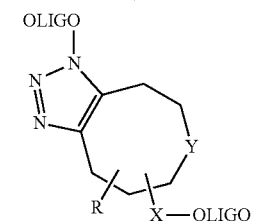

wherein X is a linker that attaches the strained alkyne group to the 3'-adapter molecule or nucleic acid; Y is one or more carbon or heteroatoms; R is an optional substituent to the ring or an electron withdrawing group; and OLIGO is the 3'-adapter molecule or the nucleic acid fragment.

The alkyne group may be strained by being part of a ring, for example a cycloalkyne such as a cyclooctyne. In particular a dibenzocyclooctyne is highly suitable for use attached to oligonucleotides that are used in fast SPAAC reactions with azides attached to oligonucleotides. The conjugated aromatic rings impose ring strain and electron withdrawing properties on the alkyne, making it react very quickly with azides. Substituents to the ring may be used to increase or decrease the reactivity of the alkyne. The strained alkyne group may comprise a substituted cyclooctyne.

Suitable cycloalkynes for use may be those that are stable at room temperature and/or stable in water, and/or stable in air. In one embodiment cycloalkynes used may be those that do not require to be stored or reacted under argon.

The strained alkyne used in the present invention may be any strained alkyne group. In one embodiment the strained alkyne may be within a ring structure, for example a cycloalkyne or a cyclic compound where the ring comprises carbon atoms and one or more heteroatoms, for example, one or more nitrogen, sulphur or oxygen atoms in the ring. The strained alkyne group may comprise a 7 to 9 membered ring. The strained alkyne group may comprise a substituted 7 to 9 membered ring. In one embodiment the strained alkyne may comprise an 8 membered ring, or a substituted 8 membered ring. The substituted or unsubstituted 8 membered ring may comprise 8 carbon atoms in the ring or may comprise one or more nitrogen, sulphur or oxygen atoms in the ring in addition to carbon atoms. The strained alkyne group may comprise a cyclooctyne. The strained alkyne group may comprise a substituted cyclooctyne. The strained alkyne group may comprise a cyclic compound having at least one heteroatom in the ring. The strained alkyne group may comprise a dibenzocyclooctyne (DIBO) group. The heteroatom may be at any position in the ring. In one embodiment there is one heteroatom in the ring.

It is advantageous to provide a strained alkyne that is reactive enough to perform the SPAAC reaction under laboratory conditions, for example because it can react in water or buffer at normal room temperature, for example 20° C., but that is also stable under laboratory conditions, for example it is stable in water, oxygen stable and stable at normal room temperature.

Figure 19:
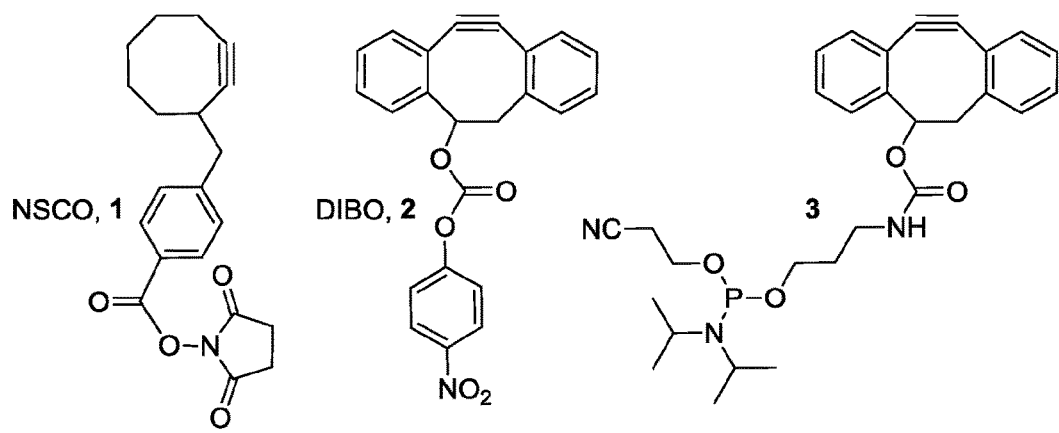
FIG. 19: shows (NSCO, 1 and DIBO 2) activated cyclooctyne carboxylic acids for labelling amino-modified oligonucleotides and (3) DIBO phosphoramide for insertion during solid-phase oligonucleotide synthesis.
Figure 20:
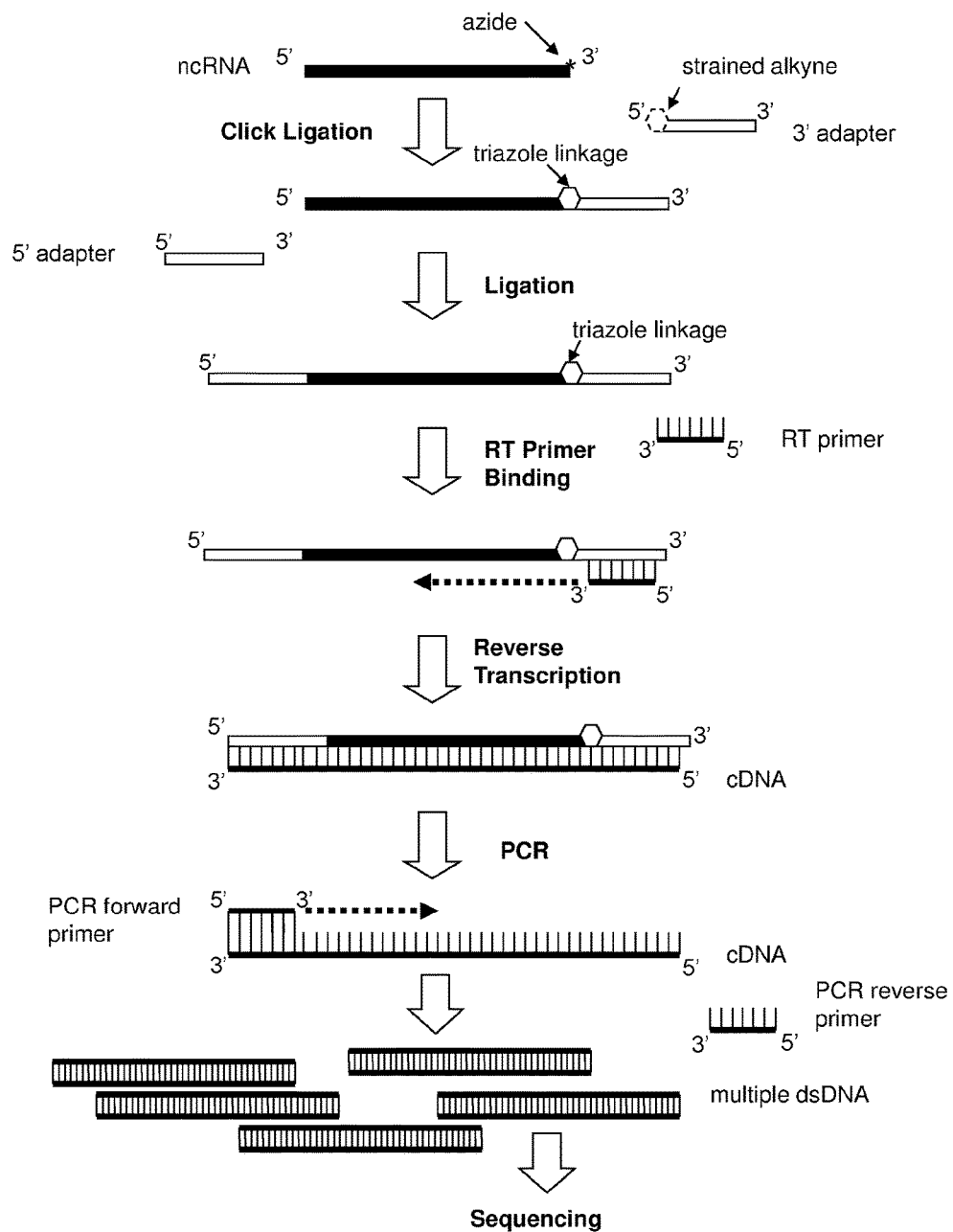
FIG. 20: shows a schematic diagram of a ncRNA sequencing reaction according to a method according to certain aspects of the present invention.

In one embodiment the strained alkyne group may comprises an unsubstituted ring, for example the strained alkyne group may be a NSCO group as shown at "1" in FIG. 19.

The following strained alkyne groups provide examples of strained alkyne groups that can be added to the end of nucleic acids or 3'-adapter molecules as active esters or phosphoramidite monomers: a nucleic acid or 3'-adapter molecule linked to a strained alkyne group wherein the strained alkyne group comprises a substituted or un-substituted cyclooctyne; a nucleic acid or 3'-adapter molecule linked to a strained alkyne group, wherein the strained alkyne group comprises a cyclooctyne having at least one heteroatom in the ring; a nucleic acid or 3'-adapter molecule linked to a strained alkyne group, wherein said strained alkyne group is a DIBO group; a nucleic acid or 3'-adapter molecule linked to a strained alkyne group, or an azide group wherein the strained alkyne group or the azide group is linked to the end of the nucleic acid fragment or 3'-adapter molecule; a nucleic acid or 3'-adapter molecule linked to a strained alkyne group or an azide group, wherein the strained alkyne group or the azide group is linked to the 3' end of the nucleic acid fragment or 5' end of the 3'-adapter molecule.

The alkyne group may be selected from the following cyclooctyne or dibenzocyclooctyne groups and may be linked to the 3'-adapter molecule or nucleic acid fragment through the groups shown below, in particular active carbonates or phosphoramidite monomers:

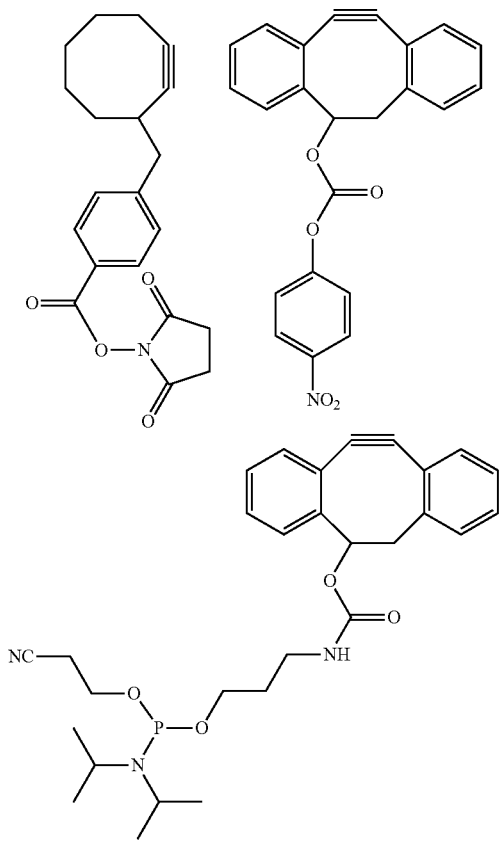

In one embodiment the ring comprising the strained alkyne is substituted with one or more groups. In one embodiment the strained alkyne group may comprise a ring with one or more substituents to the ring, for example, the strained alkyne group may comprise a dibenzocyclooctyne (DIBO) group as shown at "2" and "3" in FIG. 19. Substituent groups may be electron-withdrawing groups, groups that increase or decrease the reactivity of the alkyne. In one embodiment the ring may be fused with one or more conjugated rings, for example one or more benzene rings. In one embodiment a substituent group may comprise one or more electronegative atoms, for example fluorine.

The alkyne group may be sufficiently reactive because of the ring strain to react with the azide group without metal ion catalysis, for example, without $Cu^I$ catalysis. The reaction may proceed in a range of buffers. The reaction may go to completion within a short time scale, for example less than 1 hour, without $Cu^I$ catalysis. The reaction may go to completion within less than 30 minutes, without $Cu^I$ catalysis. The reaction may go to completion within less than 10 minutes, or less than 1 minute, or less than 30 seconds, without $Cu^I$ catalysis. The reaction may go to completion within less than 10 seconds, without $Cu^I$ catalysis. The reaction may occur at room temperature, for example 20° C. The reaction may occur at a temperature between 5 and 40° C. The reaction may occur at a temperature between 10 and 30° C., or between 15 and 25° C., or at about 20° C. The higher the reaction temperature the faster the reaction may proceed.

A strained alkyne group or an azide group may be linked to an oligonucleotide by a linker. In one embodiment the linker, shown at "X" in formulas (I), (II) and (III) links the alkyne group to the 3' end of a nucleic acid fragment or 5' end of a 3'-adapter molecule. In one embodiment the linker, shown at "X" in the above general scheme links the alkyne group to the 3' end of a nucleic acid fragment or 3'-adapter molecule. In one embodiment the alkyne group comprises the linker, the ring comprising the strained alkyne (strained alkyne ring) and all of the substituents to the alkyne ring. The linker may comprise all of the structure between the alkyne ring and the oligonucleotide that the strained alkyne group is linked to.

A linker may be a spacer that allows the strained alkyne and azide to approach each other to react. In order to allow post-synthetic labeling of the oligonucleotide the linker may have a reactive group on it such as an active ester. In this method of labeling the active ester of a strained alkyne, for example a cyclo-octyne group, may be reacted with an amino group that has been added to a 3'-adapter molecule or nucleic acid fragment. The linker attached to the cyclo-octyne may also have a phosphoramidite group attached, or another suitable group for adding monomers to 3'-adapter molecules by the phosphoramidite or H-phosphonate or phosphotriester method of oligonucleotide synthesis. In all the methods described above either single or multiple alkyne groups, for example cyclo-octyne groups can be added to a 3'-adapter molecule or nucleic acid fragment.

Linkers may be of different lengths that are appropriate to form the required link. If a spacer is too long it may slow down the reaction between a strained alkyne group and an azide group, if a linker is too short it may inhibit reaction between a strained alkyne group and an azide group as they may not be able to reach each other. A linker may be chosen for each of the strained alkyne and the azide that are to be linked to each other so that the linkers are the appropriate length to allow the strained alkyne group and the azide group to react with each other to join the nucleic acid fragment and 3'-adapter molecule. In one embodiment, a hydrophilic spacer such as (CH2CH2O)n might be used instead of a hydrophobic spacer such as (CH2)n.

The linking of the 3'-adapter molecule to the nucleic acid fragment may be carried out in metal-ion free conditions. The linking of the 3'-adapter molecule to the nucleic acid fragment may be carried out in copper-free conditions.

The linking of the 3'-adapter molecule to the nucleic acid fragment may be carried out in a salt free medium. The linking of the 3'-adapter molecule to the nucleic acid fragment may be carried out at a salt concentration of between about 0 M and about 4 M. The linking of the 3'-adapter molecule to the nucleic acid fragment may be carried out at pH of between about 5 and about 10.

The linking of the 3'-adapter molecule to the nucleic acid fragment may be a template-mediated nucleic acid ligation, for example in an embodiment where the nucleic acid fragment sequence is known.

The linking of the 3'-adapter molecule(s) to the nucleic acid fragment may not be carried out by a DNA ligase enzyme.

The adapter molecule(s) may be labelled. The adapter molecule(s) may be labelled with a fluorophore. The adapter molecule(s) may be affinity tagged for isolating the molecule on a solid phase. The linking of the adapter molecule(s), the reverse transcription, and/or the PCR may be carried out on a solid phase.

The azide group may be added to the nucleic acid fragment by use of a nucleotidyl transferase, such as a Poly(A) Polymerase (PAP) to provide an azide-modified nucleotide residue. A terminal transferase may be used to add the azide group. Yeast PAP may be used to add the azide group.

The alkyne group may be added to the 3'-adapter molecule by a phosphoramidite reaction. The alkyne group may be added to the 3'-adapter molecule by solid-phase synthesis. The alkyne group may be added to the 3'-adapter molecule by reaction with an activated nucleic acid, for example and amino-modified nucleic acid, with an active ester or carbonate of an alkyne.

The alkyne group may be added to the 3'-end of the nucleic acid fragment. The alkyne group may be added to the 3'-end of the nucleic acid fragment using a terminal transferase, such as PAP, to add an alkyne-modified nucleotide.

An azide group may be added to the 5'-end of the 3'-adapter molecule. An azide group may be added the 5'-end of the 3'-adapter molecule as an active ester to an amino-modified adapter, or added as an iodo, or bromo or mesyl-group that can be converted to azide by reaction, for example with sodium azide.

The reverse transcriptase may be RNase H deficient. The reverse transcriptase may be thermostable, for example, operating at temperatures greater than 50° C. The reverse transcriptase may comprise M-MuLV reverse-transcriptase (wild type, NEB® #M0253). In one embodiment, the reverse transcriptase comprises M-MuLV reverse-transcriptase (RNase H⁻) (mutant type, NEB® #M0368). The mutation reduces RNase H activity compared to wild type enzyme and minimizes its ability to degrade RNA.

The reverse transcription reaction may use a buffer. The reverse transcription reaction may comprise the use of a divalent cation in the buffer. The buffer may comprise $Mn^{2+}$. The buffer may comprise $Mn^{2+}$ and no $Mg^{2+}$. The buffer may comprise $Mn^{2+}$ and $Mg^{2+}$.

A buffer comprising $Mn^{2+}$ instead of $Mg^{2+}$, surprisingly and advantageously allows a faster reverse transcriptase reaction, for example a complete reaction in about 2 hours instead of 12 hours or more.

The reverse transcription reaction may be completed in less than 2 hours. The reverse transcription reaction may be completed in less than 3 hours. The reverse transcription reaction may be completed in less than 5 hours. The reverse transcription reaction may be completed in less than 8 hours.

The primer may be suitable for facilitating the reverse transcriptase polymerisation reaction during transcription. The primer may comprise or consist of any of the group comprising RNA; DNA; and a nucleic acid analogue; or combinations thereof. The primer may be arranged to hybridise to the adapted nucleic acid molecule at a site at least +1 upstream to the 3' side of the triazole linkage. The primer may be arranged to hybridise to the adapted nucleic acid molecule at a site at least +2, +3, +4 or +5 upstream to the 3' side of the triazole linkage. The primer may be arranged to hybridise to the adapted nucleic acid molecule at a site at least +6 upstream to the 3' side of the triazole linkage. The primer may be arranged to hybridise to the adapted nucleic acid molecule at a site at least +7 upstream to the 3' side of the triazole linkage. The primer may be arranged to hybridise to the adapted nucleic acid molecule at a site at least −1 residue downstream to the 5' side of the triazole linkage. The site of hybridisation may be defined as the residue at which a polymerase or reverse transcriptase would add nucleotides to extend the 3' end of the primer.

The primer may be arranged to hybridise to the adapted nucleic acid molecule at a site at least 1 residue away from the triazole linkage. The primer may be arranged to hybridise to the adapted nucleic acid molecule at a site such that the 3' end residue of the primer is at least 2, 3, 4 or 5 residues in distance towards the 3' side of the triazole linkage. The primer may be arranged to hybridise to the adapted nucleic acid molecule at a site such that the 3' end residue of the primer is at least 6 residues in distance towards the 3' side of the triazole linkage. The primer may be arranged to hybridise to the adapted nucleic acid molecule at a site such that the 3' end residue of the primer is at least 7 residues in distance towards the 3' side of the triazole linkage. The primer may be arranged to hybridise to the adapted nucleic acid molecule at a site such that the 3' end residue of the primer is at least 1 residue in distance towards the 5' side of the triazole linkage.

According to another aspect of the invention, there is provided the use of reverse transcriptase to transcribe nucleic acid comprising one or more triazole linkages.

According to another aspect of the invention, there is provided a kit for sequencing a nucleic acid fragment comprising a reverse transcriptase; and an 3'-adapter molecule having a reactive group arranged to form a triazole linkage with an opposing reactive group on the nucleic acid fragment.

The triazole linkage and reactive group arranged to form the triazole linkage may be as described herein in respect to other embodiments and aspects of the invention.

The nucleic acid fragment may be RNA. The nucleic acid fragment may be ncRNA (small RNA). The nucleic acid fragment, such as ncRNA, may be less than 200 nucleotides in length.

The reactive group may comprise one of an alkyne group or azide group. The alkyne group may be arranged to form a triazole linkage with an azide group on an opposing nucleic acid fragment or 3'-adapter molecule.

The kit may further comprise a 5'-adapter molecule. The kit may further comprise a 5'-adapter molecule and ligase.

The kit may further comprise dNTPs. The kit may further comprise a polymerase suitable for PCR. The kit may further comprise a pair of PCR primers. At least one primer may be complementary to a region of the 3'-adapter molecule or 5'-adapter molecule or the complementary sequence thereof.

The kit may further comprise one or more primers for the reverse transcriptase polymerisation. The one or more primers may be complementary to a region of the 3'-adapter molecule. The one or more primers may be capable of hybridising to the 3'-adapter molecule under stringent conditions.

The kit may further comprise a nucleotidyl transferase, such as a Poly(A) Polymerase (PAP), for adding the azide group to the nucleic acid fragment or 3'-adapter molecule. the PAP may comprise a yeast PAP. The kit may further comprise nucleoside triphosphates. The kit may further comprise modified nucleoside triphosphates having an azide or alkyne group anchored thereon.

The kit may further comprise instructions for sequencing the nucleic acid fragment.

The skilled person will understand that optional features of one embodiment or aspect of the invention may be applicable, where appropriate, to other embodiments or aspects of the invention.

Example 1—Reverse Transcription Through a Bulky Triazole Linkage—Implications for RNA Isolation and Sequencing A ncRNA molecule may be sequenced using click ligation and reverse transcription. The 3' end of a ncRNA fragment is modified with 2'azide using yeast PAP enzyme.

To apply the CuAAC reaction to sequencing, a method is required to add the alkyne or the azide function to the native RNA pool. Also the formed triazole linkage has to be compatible with the reverse transcriptase enzyme. With the correct choice of alkyne and azide a DNA backbone mimic can be read through by DNA and RNA polymerases and is functional in vivo (FIG. 13). This is despite the fact that the triazole linkage bears no obvious resemblance to a phosphodiester group. NMR studies show that the DNA duplex around the artificial backbone is similar in overall shape to normal DNA, but slightly unstable with a greater rate of opening of the base pairs. The decreased stability of DNA duplexes that contain triazole linkages (i.e. lowering of duplex melting temperature) has been addressed by the use of a modified nucleobase (G-clamp) at the triazole site that restores duplex stability. The combined nucleobase/backbone modification maintains biocompatibility and can be read through by DNA polymerase enzymes.

The biocompatibility of a triazole mimic of the DNA phosphodiester linkage in *Escherichia coli* has been evaluated via a plasmid containing click DNA backbone linkages in each strand of the gene encoding the fluorescent protein mCherry. The effect of proximity of the click linkers on their biocompatibility was also primered by placing two click DNA linkers 4-bp apart at the region encoding the fluorophore of the fluorescent protein. Very recently the biocompatibility of this triazole linkage in mammalian cells was reported. This was the first example of a non-natural DNA linkage being functional in mammalian cells. RNA strands can also be ligated by the CuAAC reaction, hammerhead ribozymes assembled by click ligation are biologically active, even when the modification is placed near the active site.

It is reported for the first time that reverse transcriptase can read through a triazole backbone which was synthesized via a CuAAC click ligation. More surprisingly, a more bulky backbone, synthesized by the copper free click ligation, was read through as well by the reverse transcriptase. Therefore, click chemistry could be considered a viable approach to the chemical ligation of RNA or DNA adaptors to natural RNA in the HTS sequencing including Illumina® SOLiD® and Roche® 454 platforms.

Discussion

Reverse transcription templates were synthesized via click chemistry using the $Cu^I$-catalysed [3+2] Azide-Alkyne Cycloaddition (CuAAC) reaction or the Strain-Promoted Alkyne Azide Cycloaddition (SPAAC) reaction between azide and cyclooctyne-modified oligonucleotides (copper-free click ligation).

RNA Templates Via the CuAAC Click Reaction

Figure 2:
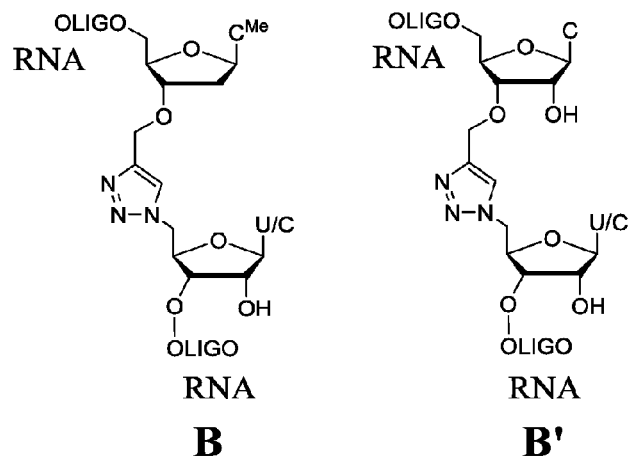
FIG. 2: $C_zU$ and $C_zC$ triazole linkages formed by CuAAC click reaction.
Figure 3:
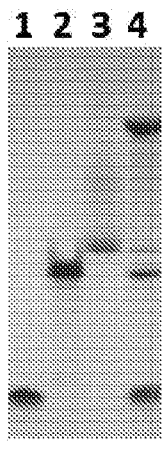
FIG. 3: 20% Polyacrylamide gel for templated CuAAC click ligation to synthesize ODN1. Lane 1; splint ODN4, lane 2; 5'-azide oligo ODN3, lane 3; alkyne oligo ODN2, lane 4; crude reaction mixture.

RNA template ODN1 (for all oligonucleotide sequences, see table 1) with the C-triazole-U linkage ($C_zU$, B) (FIG. 2) in the middle was synthesized using the CuAAC reaction. Templated click ligation of the 3'-propargyl $^{Me}dC$ oligonucleotide ODN2 (miR-155) and the 5'-azideU oligonucleotide ODN3 using splint ODN4 afforded the transcription template in a good yield (FIG. 3). Similar results were obtained when template ODN-5 was synthesised using 3'-propargyl 5'$^{Me}C$ instead of 3'-propargyl 5'$^{Me}C$ (B').

The 3'-alkyne oligonucleotides were made entirely by the phosphoramidite method. The functionalised resin required for the solid-phase synthesis of oligonucleotides terminating with 3'-propargyl $^{Me}dC$ was prepared from thymidine as previously described or 3'-propargyl C which was purchased from Glen Research. The 5'-azide oligonucleotide was synthesised using normal solid phase synthesis then the 5'-azide group was introduced in a 2-stage process; the 5'-OH group of the support-bound oligonucleotide was first converted to 5'-iodo using methyltriphenoxyphosphonium iodide then the resultant 5'-iodo oligonucleotide was reacted with sodium azide to complete the transformation.

To study the reverse transcription compatibility of these backbones, M-MuLV reverse-transcriptase (wild type, NEB® #M0253) as well as M-MuLV reverse-transcriptase (RNase H⁻) (mutant type, NEB® #M0368) were used. The mutant M-MuLV reverse-transcriptase (RNase H⁻), an enzyme frequently used for RNA sequencing applications, is an engineered enzyme with reduced RNase H activity comparing to wild type enzyme. The mutation minimizes its ability to degrade the RNA.

Five DNA primers of different lengths were designed and used for the reverse transcription of the two RNA triazole templates, ODN1 and ODN5 ($C_zU$). When the primers anneal to the template, they generate reverse-transcription starting points (at the 3'-end) far before ODN7 (−7, P1) and ODN8 (−3, P2), just before ODN9 (+0, P3), 1 nucleotide after ODN10 (+1, P4) and 4 nucleotides after ODN11 (+4, P5) the triazole point. In the last two cases the triazole is bridged by the primers.

Figure 4:
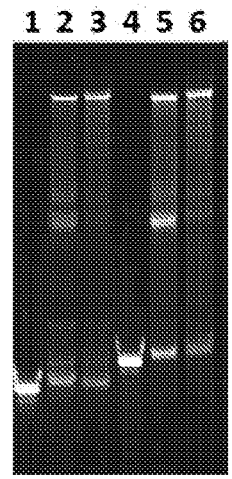
FIG. 4: Reverse Transcription of the triazole template ODN5 (Backbone B') ($C_zU$) by M-MuLV reverse-transcriptase (RNase H⁻) (NEB®) in $Mg^{2+}$-buffer. Lane 1; primer (ODN10) (+1, P4), lane 2 and 3; reverse transcription product of click template (ODN5) and control template (ODN12) using primer (ODN10), lane 4; primer (ODN11) (+4, P5), lane 5 and 6 reverse transcription product of click template (ODN5) and control template (ODN12) using primer (ODN11).
Figure 5:
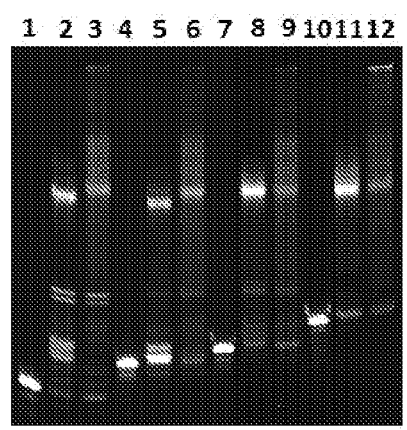
FIG. 5: Reverse transcription of the control template ODN12 and click template ODN5 (backbone B') ($C_zU$) by M-MuLV reverse-transcriptase (RNase H⁻) in 3 mM $Mn^{2+}$ buffer. Lane 1; ODN8(P2), lane 4; ODN9(P3), lane 7; ODN10(P4), lane 10 ODN11(P5), lanes 2, 5; 8 and 11 are reverse transcription of click template ODN5, lanes 3, 6, 9 and 12 are reverse transcription of native RNA template ODN12.
Figure 6:
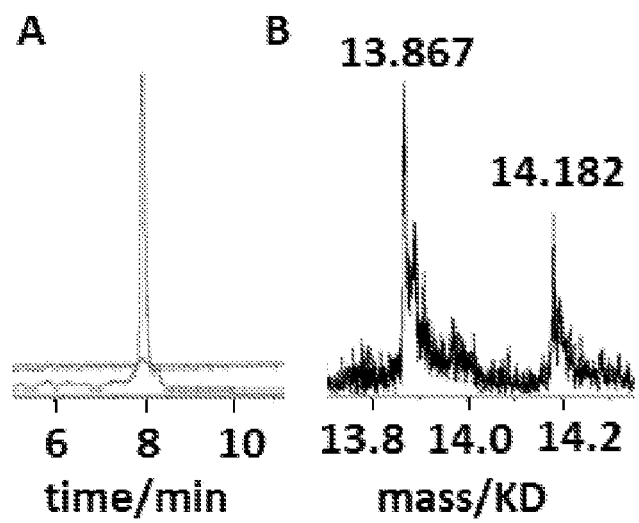
FIG. 6: (A) HPLC and (B) mass spectroscopy, of the M-MuLV reverse transcriptase (RNase H⁻) products of the triazole template ODN5 (backbone B') (minus "G", cal. 13867), (minus "G" plus "A", cal. 14180). The "plus A" fragment was likely resulted from the terminal transferase activity of the reverse-transcriptase. (6 mM $Mn^{2+}$ and primer ODN7 (−7, P1) were used).
Figure 7:
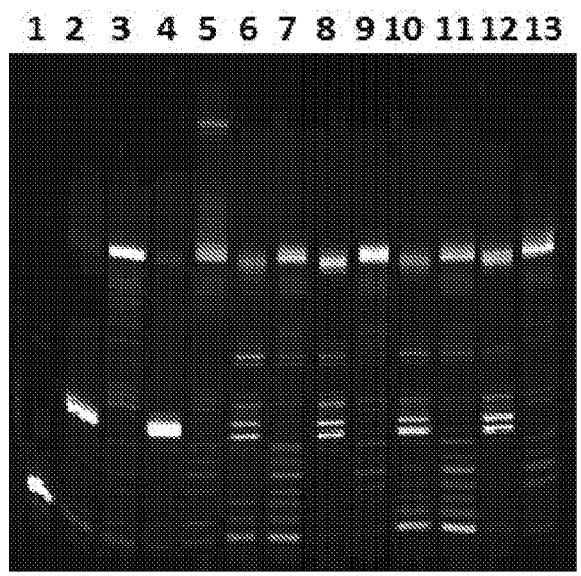
FIG. 7: 20% polyacrylamide gel for the effect of $Mg^{2+}$/$Mn^{2+}$ concentrations on the reverse transcription of ODN5 ($C_zU$) (B') and control ODN12 respectively. Lane 1, primer ODN7(−7, P1), lane 2 and 3; 3 mM $Mg^{2+}$ (1 eq of primer) lane 4 and 5; 3 mM $Mg^{2+}$ (2 eq of primer), lane 6 and 7; 3 mM $Mg^{2+}$+3 mM $Mn^{2+}$ (1 eq of primer), lane 8, 9; 3 mM $Mg^{2+}$+3 mM $Mn^{2+}$ (2 eq of primer), lane 10 and 11; 3 mM $Mn^{2+}$ (1 eq of primer), lane 12 and 13; 3 mM $Mn^{2+}$ (2 eq of primer). M-MuLV reverse transcriptase (wild type) was used for 1 h. at 37° C.
Figure 8:
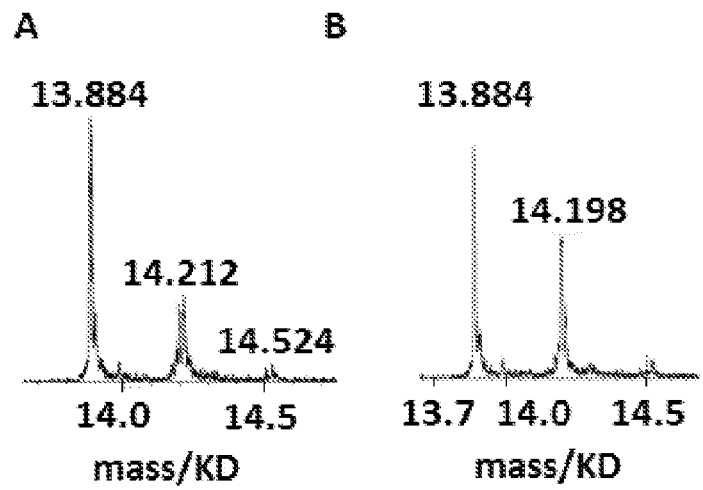
FIG. 8: Mass spectroscopy of reverse transcriptase product using $C_zC$ templates (A) ODN13 and (B) ODN14. M-MuLV reverse transcriptase (wild type) with 3 mM $Mg^{2+}$ and primer ODN7 were used, incubated at 37° C. for 2 h then desalting by gel-filtration (NAP-10). Cal. Mass: 14212 (full length); 14525 (full length plus A); 13883 (minus G); 14196 (minus G plus A).
Figure 9:
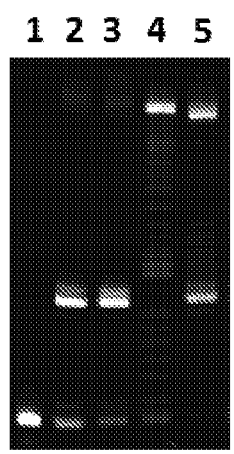
FIG. 9: 20% polyacrylamide gel for reverse transcription of $C_zU$ ODN5 (B') and ODN1 (B) and $C_zC$ ODN13 (B'). M-MuLV reverse transcriptase (wild type), 3 mM $Mg^{2+}$, lane 1; primer ODN7, lane 2; reverse transcription of ODN5 (B', $C_zU$), lane 3; reverse transcription of ODN1 (B, $C_zU$), lane 4; reverse transcription of control ODN15, lane 5; reverse transcription of ODN13 ($C_zC$, B').

The reverse transcription of the triazole templates ODN1 and ODN5 stopped at the triazole site when primers P1 and P2 and P3 were used, while it gave the full length product when bridged primers P4 and P5 were used (FIG. 4). Addition of $Mn^{2+}$ to the $Mg^{2+}$ buffer allowed the reverse transcriptase to read through the triazole even with the non-bridged primers P1, P2 and P3. The non-bridged primers gave a mixture of full-length product and (minus G) product as shown by PAGE and mass spectroscopy (FIGS. 5 and 6).

The inability of the reverse transcriptase to read through the triazole linkage efficiently in the presence of $Mg^{2+}$ could be due to the instability of the duplex formed between the triazole template and the primer. Therefore it was of interest to change the bases around the triazole linkage to $C_zC$ instead of $C_zU$ to give a more stable template/primer duplex. Accordingly, two templates ODN13 and ODN14 with C-triazole-C($C_zC$) instead of ($C_zU$) were synthesized via the CuAAC click ligation. As expected, M-MuLV reverse transcriptase read through the $C_zC$ triazole linkages in $Mg^{2+}$ buffer using the 5 primers mentioned above. This indicates that the $C_zC$ triazole linkage template formed a more stable duplex than the $C_zU$ linkage to allow the reverse transcriptase to carry on reading the template and pass through the triazole linkage.

RNA/RNA Templates and RNA/DNA Chimera Via the SPAAC Copper Free Click Reaction

The copper-free AAC reaction on DNA has potential advantages when compared to the CuAAC reaction, especially in RNA click ligation. As it does not require catalysis with toxic metals, it has potential uses in vivo and in RNA click ligation. However, the reaction between azides and unactivated terminal alkynes is very slow in the absence of $Cu^I$ catalysis, even when templated by DNA. However, the copper-free reaction can be accelerated by using an alkyne which is distorted by incorporation into an 8-membered ring structure. The ring-strain promoted alkyne-azide [3+2] cycloaddition reaction (SPAAC reaction) has been pioneered by Bertozzi, principally for in vivo labelling of carbohydrates. It has recently been applied to DNA strand ligation, using dibenzocyclooctyne (DIBO) or bicyclo [6.1.0]nonyne (BCN) as the strained alkynes.

Both DIBO and BCN chemistries are commercially available, the click ligation using DIBO produces four diastereoisomers, originating from the two enantiomers of DIBO and the two triazole regioisomers, while BCN produces just two enantiomeric products. In addition, the BCN triazole linker is more likely to be accommodated by the reverse transcriptase enzyme. Therefore it was decided to use the BCN chemistry for the copper free synthesis of templates and to evaluate them in reverse transcription reactions.

Two RNA templates ODN19 and ODN20 with $U_zC$ and $C_zC$ in the middle were synthesised by the copper free SPAAC reaction by ligation of 5'-BCN oligonucleotide ODN21 with 2'-azide oligonucleotides ODN22 or ODN23.

Figure 12:
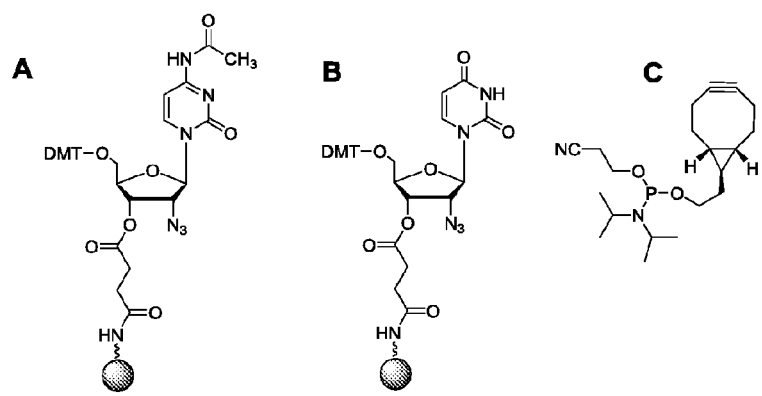
FIGS. 12: A and B) are 5'-O-(4,4'-dimethoxytrityl)-2'-azido-2'-deoxycytidine (N-Ac) and 5'-dimethoxytrityl)-2'-azido-2'-deoxyuridine functionalized resins for the synthesis of 2'-azido model RNAs respectively. C) BCN phosphoramidite for 5' labelling of the 3'-adapter.

The key building blocks for the synthesis of the 2'-azide labelled model RNA strands are 5'-O-(4,4'-Dimethoxytrityl)-2'-azido-2'-deoxyuridine or 5'-O-(4,4'-dimethoxytrityl)-2'-azido-2'-deoxycytidine. These were made and coupled to succinylated aminoalkyl solid support to give the derivatised supports which were used in the solid-phase synthesis of 2'-azide oligonucleotides (FIG. 12). To synthesis the alkyne oligonucleotide ODN21, BCN phosphoramidite (FIG. 12) was added to the 5'-terminus during solid-phase synthesis. This was reacted with the 2'-azide oligonucleotides in water to form the RNA templates ODN19 and ODN20 in very good yield (FIG. 13). For ease of purification, no template was used and instead very concentrated reaction mixtures were employed to ensure good yields.

Because the BCN linker generated in the SPAAC reaction is much bulkier than the triazole link generated by CuAAC, it was expected that it would hinder the reverse transcriptase. Consequently, Click BCN backbones were reverse-transcribed overnight using M-MuLV Reverse Transcriptase (RNase H⁻) instead of M-MuLV Reverse Transcriptase (wild type) to avoid the degradation during overnight incubation. The template with the $C_zC$ linkage was investigated before the $U_zC$ linkage as it was expected to give more stable duplex with the primer. After 2 h incubation at 37° C., both PAGE and MS showed that the M-MuLV Reverse Transcriptase (RNase H⁻) paused at the triazole site ($C_zC$) but then read-through this site successfully during overnight incubation (FIG. 14, lane 5 and 6). The MS of the 2 h incubation sample showed two HPLC peaks representing "stopped before triazole" and "Full-length minus G" ("−G") products. After overnight incubation, the "Stopped before triazole" product disappeared. Most of the primer extended to the end of the template and produced the "Full-length-G+A" product. This "+A" was likely added at the 3' end of the DNA product during the overnight reaction.

Changing the divalent cation in the buffer from $Mg^{2+}$ to $Mn^{2+}$ allowed the reverse transcription reaction to be nearly completed in 2 h instead of overnight (FIG. 15A). The MS confirmed that under this condition the same (full length minus G plus A) product was obtained (FIG. 15B).

Figure 10:
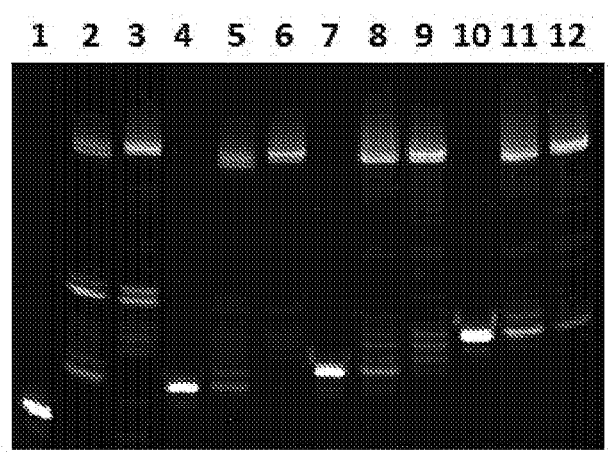
FIG. 10: 20% polyacrylamide gel for reverse transcription of ODN14 ($C_zC$, B). M-MuLV Reverse Transcriptase (Wild type) in $Mg^{2+}$ buffer at 37° C. for 2 h. Lane 1, 2 and 3; primer ODN8, (−3, P2) and the reverse transcription of triazole ODN14 and control ODN15 using it, lane 4, 5 and 6; primer ODN16 (+0, P6) and the reverse transcription of triazole ODN14 and control ODN15 using it; lane 7, 8 and 9; primer ODN17 (+1, P7) and the reverse transcription of triazole ODN14 and control ODN15 using it; lane 10, 11 and 12; primer ODN18 (+4, P8) and the reverse transcription of triazole ODN14 and control ODN15 using it.
Figure 11:
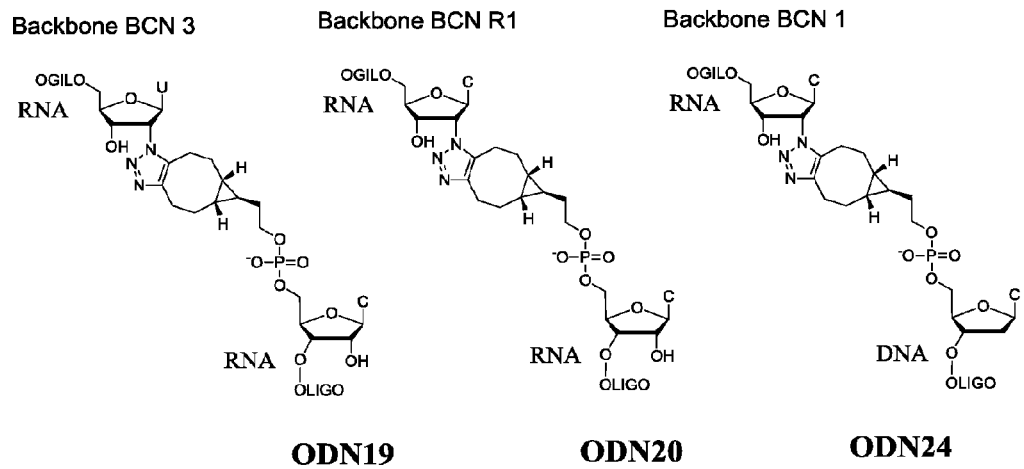
FIG. 11: Triazole backbones formed via copper free click chemistry.
Figure 16:
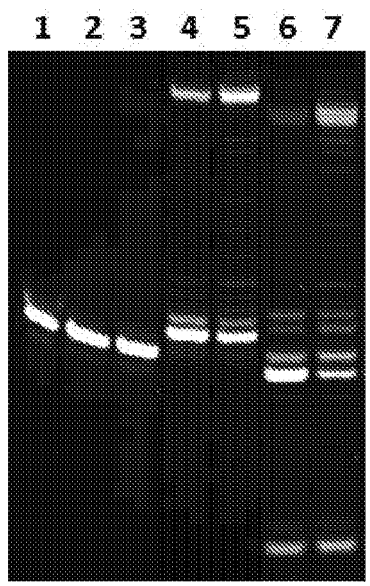
FIG. 16: 20% polyacrylamide gel for reverse transcription of ODN20 BCN R1. Lane 1; ODN26 (+T, P9), lane 2 and 3; reverse transcription after 2 h and 7 h using primer ODN26, lane 4 and 5; reverse transcription after 2 h and 7 h using primer ODN27 (+T+1, P10), lane 6 and 7; reverse transcription after 2 h and 7 h using primer ODN7.

Comparing the efficiency of the reverse transcriptase reaction using the bridged primer (+1) and the (−7) primer, it was found that the one which started far before the triazole site worked more efficiently than the bridged one. This indicates that it is easier for the reverse transcriptase to pass the triazole-BCN link during polymerization than to start near the triazole-BCN link. These results were expected due to the length and bulkiness of the BCN backbone, and were different than those obtained from using the bridged primers with the biocompatible triazole linkage $C_zC$ (ODN14) (FIG. 10). Addition of an extra base to the primer opposite the BCN ring might help the bridged primer to work with the bulky linkage. Two primers (+T) with (T) opposing the triazole-BCN linkage or (+T+1) were investigated. Interestingly, the results showed that the "+T" primer cannot extend further and the "+T+1" primer gave similar results to those obtained from the short (−7) primer with the 3' end 7 bases before the triazole (FIG. 16). It is known that the polymerisation may omit a residue at the region of the triazole linkage which can be taken into account in the sequence determination.

Figure 17:
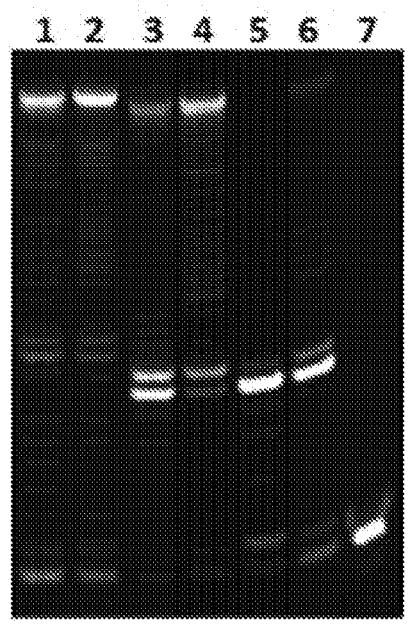
FIG. 17: 20% polyacrylamide gel for reverse transcription of ODN24 BCN 1. Lane 1 and 2; reverse transcription of control ODN15 after 2 h and 16 h using 3 mM $Mn^{2+}$, lane 3 and 4; reverse transcription of triazole template ODN24 after 2 h and 16 h using 3 mM $Mn^{2+}$, lane 5 and 6; reverse transcription of triazole template ODN24 after 2 h and 16 h using 3 mM $Mg^{2+}$, lane 7; primer ODN7.

Both DNA and RNA have been used as 3'-adaptors for RNA ligation. However, it was found that the M-MuLV reverse transcriptase reads through DNA/RNA junctions less efficiently than it reads through RNA/RNA junctions. The Backbone BCN1 with DNA adaptor instead of RNA adaptor was synthesized for reverse transcription. Comparing to Backbone BCN R1 with RNA adaptor, the reverse transcription of Backbone BCN1 (ODN24) was significantly less efficient (FIG. 14, lane 1 and 2). Addition of $Mn^{2+}$ to the buffer significantly improved the reverse transcription of Backbone BCN1. However, the reverse transcription of Backbone BCN R1 was still faster as finished in 2 h in $Mn^{2+}$ buffer (FIG. 15) compared to 16 h in the case of BCN1 (FIG. 17).

The Backbone BCN3 with the sequence "$U_zC$" instead of "$C_zC$" (Backbone BCN R1) was also investigated. It was expected not to give very good results as it might give a less stable duplex than the corresponding $C_zC$ template. As expected, the reverse transcription of this backbone in standard $Mg^{2+}$-buffer had difficulty in passing the triazole-BCN link. The problem was not solved by using "+1" primer as it was not extended as well. The reaction buffer containing 3 mM $Mg^{2+}$ and 3 mM $Mn^{2+}$ helped the M-MuLV Reverse Transcriptase to read-through this "U-BCN-C" linkage. However, both PAGE and MS showed that the reverse transcription produced a mixture of products including two-nucleotide-deletion and one-nucleotide-deletion.

TABLE 1 oligonucleotides used in this study

| Code | Sequence (5' - 3') |
|---|---|
| ODN1 | ODN2 + ODN3 $C_zU$ Backbone B |
| ODN2 | PUUAAUGCUAAUCGUGAUAGGGGU$^{Me}C^K$, $^{Me}C^K$ = 3'-propargyl C |

TABLE 1-continued oligonucleotides used in this study

| Code | Sequence (5' - 3') |
|---|---|
| ODN3 | $^Z$UAGAUCGGAAGAGCGGUUCAG,<br>$^Z$U = 5'-azido U |
| ODN4 | CCGATCTAGACCCCTCU splint |
| ODN5 | ODN3 + ODN6 C$_z$U Backbone B' |
| ODN6 | UUAAUGCUAAUCGUGAUAGGGGUC$^K$,<br>C$^K$ = 3'-propargyl C |
| ODN7 | FCTGAACCGCTCTTC primer P$_1$ |
| ODN8 | FCTGAACCGCTCTTCCGAT primer P$_2$ |
| ODN9 | FCTGAACCGCTCTTCCGATCTA primer P$_3$ |
| ODN10 | FCTGAACCGCTCTTCCGATCTAG primer P$_4$ |
| ODN11 | FCTGAACCGCTCTTCCGATCTAGACC primer P$_5$ |
| ODN12 | UUAAUGCUAAUCGUGAUAGGGGUCUAGAUCG<br>GAAGAGCGGUUCAG |
| ODN13 | PODN6 + ODN28 C$_z$C Backbone B' |
| ODN14 | ODN2 + ODN28 C$_z$C Backbone B |
| ODN15 | UUAAUGCUAAUCGUGAUAGGGGUCCAGAUCG<br>GAAGAGCGGUUCAG |
| ODN16 | FCTGAACCGCTCTTCCGATCTG primer P6 |
| ODN17 | FTGAACCGCTCTTCCGATCTGG primer P7 |
| ODN18 | FCTGAACCGCTCTTCCGATCTGGACC primer P8 |
| ODN19 | ODN21 + ODN22 BCN3 |
| ODN20 | ODN21 + ODN23 BCN R1 |

TABLE 1-continued oligonucleotides used in this study

| Code | Sequence (5' - 3') |
|---|---|
| ODN21 | X$_7$CAGAUCGGAAGAGCGGUUCAG<br>X$_7$ = BCN monomer |
| ODN22 | PUUAAUGCUAAUCGUGAUAGGGGUU$^z$,<br>U$^z$ = 2'-azido-2'-dU |
| ODN23 | UUAAUGCUAAUCGUGAUAGGGGUC$^z$<br>C$^z$ = 2'-azido-2'-dC |
| ODN24 | ODN23 + ODN25 BCN1 |
| ODN25 | X$_7$CAGATCGGAAGAGCGGTTCAG,<br>X$_7$ = BCN monomer |
| ODN26 | FCTGAACCGCTCTTCCGATCTGT primer P9 |
| ODN27 | FCTGAACCGCTCTTCCGATCTGTG primer P10 |
| ODN28 | $^Z$CAGAUCGGAAGAGCGGUUCAG,<br>$^Z$C = 5'-azido C |

F = 5'-FAM, P = 5'-phosphate

DNA Sequencing Analysis

DNA formed from the reverse transcription of ODN19 (BCN3), ODN20 (BCNR1) and ODN15 (control) were purified by 20% polyacrylamide gel. 3 PCR reactions (50 µL) were carried out using GoTaq DNA polymerase and the extracted DNA. The PCR products were purified using a 2% agarose gel followed by extraction using QIAquick Gel Extraction kit (50) Cat. No. 28704. Cloning and sequencing of these PCR products were performed by the automated fluorescent Sanger method. With reference to FIG. 18, the results showed that the product from the reverse transcription of the triazole templates formed from the copper free click chemistry missed only one of the two bases around the triazole. However, this base is known as it would be added to the native RNA pool by Yeast PAP polymerase. 2'-Azido-dUTP and 2'-azido-dCTP was incorporated previously by Yeast PAP efficiently.

The invention claimed is:

1. A method of nucleic acid processing comprising:
providing an adapted nucleic acid fragment comprising a nucleic acid fragment linked at its 3'-end to a 3'-adapter molecule by a triazole linkage comprising a 1,2,3-triazole group, wherein the 3'-adapter molecule comprises RNA, DNA, a nucleic acid analogue or combinations thereof;
annealing a primer to the adapted nucleic acid fragment, wherein the primer anneals to a region of the 3'-adapter molecule; and
processing the adapted nucleic acid fragment by transcribing at least a portion of the adapted nucleic acid fragment with reverse transcriptase, wherein said portion of the adapted nucleic acid fragment transcribed with reverse transcriptase comprises said triazole linkage.

2. The method according to claim 1, wherein the triazole linkage is a result of $Cu^I$-catalysed [3+2] Azide-Alkyne Cycloaddition (CuAAC) reaction; or a Strain-Promoted Alkyne Azide Cycloaddition (SPAAC) reaction.

3. The method according to claim 1, wherein the adapted nucleic acid fragment comprises a 5'-adapter molecule linked to the 5'-end of the nucleic acid fragment, wherein the 5'-adapter molecule comprises RNA, DNA, a nucleic acid analogue or combinations thereof.

4. The method according to claim 1, wherein the adapted nucleic acid fragment comprises RNA or a combination of RNA and other nucleic acid, or analogues thereof.

5. The method according to claim 1, wherein the method comprises a method of nucleic acid sequencing, wherein
the adapted nucleic acid fragment is provided by:
linking the 3'-adapter molecule to the 3' end of the nucleic acid fragment, thereby forming the adapted nucleic acid fragment, wherein the 3'-adapter molecule is linked to the nucleic acid fragment via a triazole linkage; and wherein
the adapted nucleic acid fragment is transcribed by
annealing the primer to the adapted nucleic acid fragment, which is complementary thereto;
transcribing at least a portion of the adapted nucleic acid fragment using reverse transcriptase to form a cDNA strand, wherein said portion of the adapted nucleic acid fragment transcribed using reverse transcriptase comprises the triazole linkage; and
further comprising determining the sequence of the cDNA strand.

6. The method according to claim 5, further comprising linking a 5'-adapter molecule to the 5'-end of the nucleic acid fragment, optionally wherein the 5'-adapter molecule is linked to the 5'-end of the nucleic acid fragment by a ligase.

7. The method according to claim 1, wherein the 3'-adapter molecule and/or 5'-adapter molecule have a known/pre-determined sequence.

8. The method according to claim 1, wherein the nucleic acid fragment is RNA, optionally wherein the RNA comprises non-coding RNA (ncRNA).

9. The method according to claim 5, wherein determining the sequence of the cDNA strand comprises amplifying the sequence of the cDNA strand in a PCR reaction, and analyzing the PCR product.

10. The method according to claim 1 wherein, the triazole linkage comprises a 7 to 9 membered ring, and a triazole group.

11. The method according to claim 1 wherein, the triazole linkage comprises:

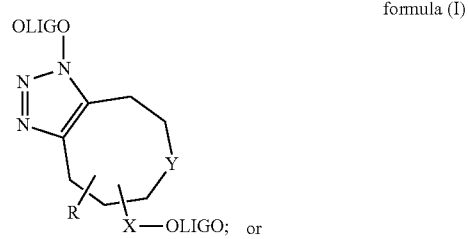

formula (I)

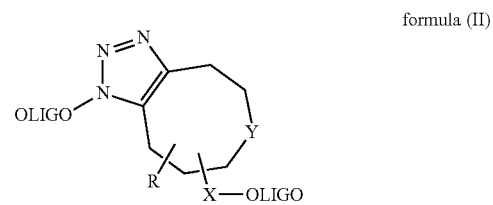

formula (II)

wherein:

X is a linker;

Y is one or more carbon or heteroatoms;

R is a substituent; and

OLIGO is the 3'-adapter molecule or the nucleic acid fragment.

12. The method according to claim 1 wherein, the adapted nucleic acid fragment having the triazole linkage comprises the formula (III):

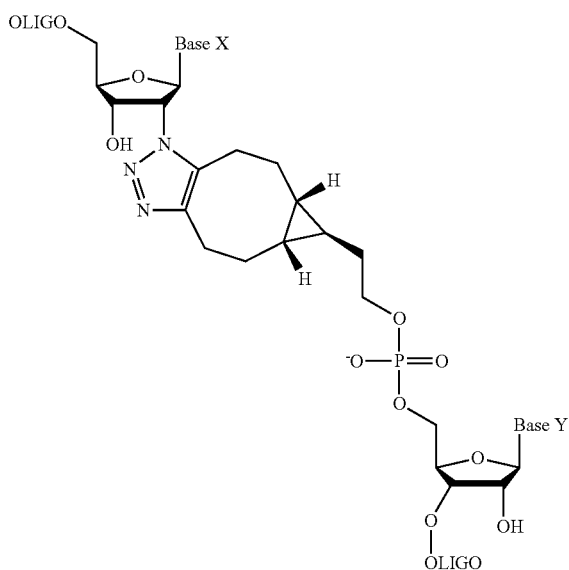

wherein:
Base X is guanine, adenine, uracil, thymine or cytosine
Base Y is guanine, adenine, uracil, thymine or cytosine; and
OLIGO is a nucleic acid fragment, or analogue thereof, or an adapter molecule.

13. The method according to claim 1 wherein the triazole linkage is formed by reacting an alkyne group on the nucleic acid fragment with an azide group on the 3'-adapter molecule; or by reacting an alkyne group on the 3'-adapter molecule with an azide group on the nucleic acid fragment.

14. The method according to claim 13, wherein the alkyne group comprises a cyclooctyne or dibenzocyclooctyne.

15. The method according to claim 1, wherein the linking of the 3'-adapter molecule to the nucleic acid fragment is carried out in metal-ion free conditions.

16. The method according to claim 1 wherein, the reverse transcriptase is RNase H deficient.

17. The method according to claim 1 wherein, the reverse transcription reaction uses a buffer comprising $Mn^{2+}$.

18. A kit for sequencing a nucleic acid fragment comprising
a reverse transcriptase; and
a 3'-adapter molecule comprising RNA, DNA, a nucleic acid analogue or combinations thereof and having a reactive group arranged to form a triazole linkage with an opposing reactive group on the nucleic acid fragment;
and wherein the reactive group comprises an azide or an alkyne group at a 5'-end of the 3'-adapter molecule,
wherein the kit further comprises:
one or more primers for reverse transcriptase polymerisation, wherein the one or more primers is each configured to anneal to a region of the 3'-adapter molecule at a site such that the 3' end of the primer is from 4 residues downstream to the 5' side of the triazole linkage to at least 1 residue upstream to the 3' side of the triazole linkage;
a resin for a solid-phase phosphoramidite reaction for adding an alkyne group to the nucleic acid fragment or 3'-adapter molecule; and
a resin for a solid-phase phosphoramidite reaction for adding an alkyne group to the nucleic acid fragment or 3'-adapter molecule.

19. The kit according to claim 18, further comprising at least one of:
a 5'-adapter molecule comprising RNA, DNA, a nucleic acid analogue or combinations thereof; and
a nucleotidyl transferase.

* * * * *

SEQUENCE LISTING

<160> NUMBER OF SEQ ID NOS: 28

<210> SEQ ID NO 1
<211> LENGTH: 45
<212> TYPE: RNA
<213> ORGANISM: Homo sapiens

<400> SEQUENCE: 1
uuaaugcuaa ucgugauagg ggucuagauc ggaagagcgg uucag          45

<210> SEQ ID NO 2
<211> LENGTH: 24
<212> TYPE: RNA
<213> ORGANISM: Homo sapiens

<400> SEQUENCE: 2
uuaaugcuaa ucgugauagg gguc          24

<210> SEQ ID NO 3
<211> LENGTH: 21
<212> TYPE: RNA
<213> ORGANISM: Homo sapiens

<400> SEQUENCE: 3
uagaucggaa gagcgguuca g                                    21

<210> SEQ ID NO 4
<211> LENGTH: 17
<212> TYPE: DNA
<213> ORGANISM: Homo sapiens

<400> SEQUENCE: 4
ccgatctaga cccctcu                                          17

<210> SEQ ID NO 5
<211> LENGTH: 45
<212> TYPE: RNA
<213> ORGANISM: Homo sapiens

<400> SEQUENCE: 5
uagaucggaa gagcgguuca guuaaugcua aucgugauag ggguc            45

<210> SEQ ID NO 6
<211> LENGTH: 24
<212> TYPE: RNA
<213> ORGANISM: Homo sapiens

<400> SEQUENCE: 6
uuaaugcuaa ucgugauagg gguc                                  24

<210> SEQ ID NO 7
<211> LENGTH: 14
<212> TYPE: DNA
<213> ORGANISM: Homo sapiens

<400> SEQUENCE: 7
ctgaaccgct cttc                                             14

<210> SEQ ID NO 8
<211> LENGTH: 18
<212> TYPE: DNA
<213> ORGANISM: Homo sapiens

<400> SEQUENCE: 8
ctgaaccgct cttccgat                                         18

<210> SEQ ID NO 9
<211> LENGTH: 21
<212> TYPE: DNA
<213> ORGANISM: Homo sapiens

<400> SEQUENCE: 9
ctgaaccgct cttccgatct a                                     21

<210> SEQ ID NO 10
<211> LENGTH: 22
<212> TYPE: DNA
<213> ORGANISM: Homo sapiens

<400> SEQUENCE: 10
ctgaaccgct cttccgatct ag                                    22

<210> SEQ ID NO 11
<211> LENGTH: 25
<212> TYPE: DNA
<213> ORGANISM: Homo sapiens

```
<400> SEQUENCE: 11
ctgaaccgct cttccgatct agacc                                      25

<210> SEQ ID NO 12
<211> LENGTH: 45
<212> TYPE: RNA
<213> ORGANISM: Homo sapiens

<400> SEQUENCE: 12
uuaaugcuaa ucgugauagg ggucuagauc ggaagagcgg uucag                45

<210> SEQ ID NO 13
<211> LENGTH: 45
<212> TYPE: RNA
<213> ORGANISM: Homo sapiens

<400> SEQUENCE: 13
uuaaugcuaa ucgugauagg gguccagauc ggaagagcgg uucag                45

<210> SEQ ID NO 14
<211> LENGTH: 45
<212> TYPE: RNA
<213> ORGANISM: Homo sapiens

<400> SEQUENCE: 14
uuaaugcuaa ucgugauagg gguccagauc ggaagagcgg uucag                45

<210> SEQ ID NO 15
<211> LENGTH: 45
<212> TYPE: RNA
<213> ORGANISM: Homo sapiens

<400> SEQUENCE: 15
uuaaugcuaa ucgugauagg gguccagauc ggaagagcgg uucag                45

<210> SEQ ID NO 16
<211> LENGTH: 21
<212> TYPE: DNA
<213> ORGANISM: Homo sapiens

<400> SEQUENCE: 16
ctgaaccgct cttccgatct g                                          21

<210> SEQ ID NO 17
<211> LENGTH: 21
<212> TYPE: DNA
<213> ORGANISM: Homo sapiens

<400> SEQUENCE: 17
ctgaaccgct cttccgatct g                                          21

<210> SEQ ID NO 18
<211> LENGTH: 25
<212> TYPE: DNA
<213> ORGANISM: Homo sapiens

<400> SEQUENCE: 18
ctgaaccgct cttccgatct ggacc                                      25

<210> SEQ ID NO 19
<211> LENGTH: 45
<212> TYPE: RNA
<213> ORGANISM: Homo sapiens
```

```
<400> SEQUENCE: 19
cagaucggaa gagcgguuca guuaaugcua aucgugauag ggguu          45

<210> SEQ ID NO 20
<211> LENGTH: 45
<212> TYPE: RNA
<213> ORGANISM: Homo sapiens

<400> SEQUENCE: 20
cagaucggaa gagcgguuca guuaaugcua aucgugauag gqquc          45

<210> SEQ ID NO 21
<211> LENGTH: 21
<212> TYPE: RNA
<213> ORGANISM: Homo sapiens

<400> SEQUENCE: 21
cagaucggaa gagcgguuca g                                    21

<210> SEQ ID NO 22
<211> LENGTH: 24
<212> TYPE: RNA
<213> ORGANISM: Homo sapiens

<400> SEQUENCE: 22
uuaaugcuaa ucgugauagg gguu                                 24

<210> SEQ ID NO 23
<211> LENGTH: 24
<212> TYPE: RNA
<213> ORGANISM: Homo sapiens

<400> SEQUENCE: 23
uuaaugcuaa ucgugauagg gguc                                 24

<210> SEQ ID NO 24
<211> LENGTH: 45
<212> TYPE: DNA
<213> ORGANISM: Homo sapiens

<400> SEQUENCE: 24
uuaaugcuaa ucgugauagg gguccagauc ggaagagcgg ttcag          45

<210> SEQ ID NO 25
<211> LENGTH: 21
<212> TYPE: DNA
<213> ORGANISM: Homo sapiens

<400> SEQUENCE: 25
cagatcggaa gagcggttca g                                    21

<210> SEQ ID NO 26
<211> LENGTH: 22
<212> TYPE: DNA
<213> ORGANISM: Homo sapiens

<400> SEQUENCE: 26
ctgaaccgct cttccgatct gt                                   22

<210> SEQ ID NO 27
<211> LENGTH: 23
<212> TYPE: DNA
```

```
<213> ORGANISM: Homo sapiens

<400> SEQUENCE: 27
ctgaaccgct cttccgatct gtg                                              23

<210> SEQ ID NO 28
<211> LENGTH: 21
<212> TYPE: RNA
<213> ORGANISM: Homo sapiens

<400> SEQUENCE: 28
cagaucggaa gagcgguuca g                                                21
```